United States Patent
Labhasetwar et al.

(10) Patent No.: US 10,016,488 B2
(45) Date of Patent: Jul. 10, 2018

(54) NITRIC OXIDE SYNTHASE NANOPARTICLES FOR TREATMENT OF VASCULAR DISEASE

(71) Applicant: THE CLEVELAND CLINIC FOUNDATION, Cleveland, OH (US)

(72) Inventors: Vinod Labhasetwar, Cleveland, OH (US); Jaspreet K. Vasir, Cleveland, OH (US); Maram K. Reddy, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 15/097,757

(22) Filed: Apr. 13, 2016

(65) Prior Publication Data

US 2016/0324935 A1 Nov. 10, 2016

Related U.S. Application Data

(60) Provisional application No. 62/146,530, filed on Apr. 13, 2015.

(51) Int. Cl.
| | |
|---|---|
| *A61K 38/44* | (2006.01) |
| *A61K 9/00* | (2006.01) |
| *A61K 9/51* | (2006.01) |
| *A61F 2/82* | (2013.01) |
| *A61K 9/48* | (2006.01) |
| *A61K 9/50* | (2006.01) |
| *A61L 29/04* | (2006.01) |
| *A61L 29/16* | (2006.01) |
| *A61L 31/04* | (2006.01) |
| *A61L 31/16* | (2006.01) |
| *A61M 25/10* | (2013.01) |

(52) U.S. Cl.
CPC .............. *A61K 38/44* (2013.01); *A61F 2/82* (2013.01); *A61K 9/0019* (2013.01); *A61K 9/4866* (2013.01); *A61K 9/5031* (2013.01); *A61K 9/5153* (2013.01); *A61L 29/048* (2013.01); *A61L 29/16* (2013.01); *A61L 31/047* (2013.01); *A61L 31/16* (2013.01); *A61M 25/10* (2013.01); *C12Y 114/13039* (2013.01); *A61F 2210/0076* (2013.01); *A61F 2310/0097* (2013.01); *A61L 2300/254* (2013.01); *A61L 2300/412* (2013.01); *A61L 2300/606* (2013.01); *A61M 2025/105* (2013.01)

(58) Field of Classification Search
CPC .................................................. A61K 9/0019
See application file for complete search history.

(56) References Cited

U.S. PATENT DOCUMENTS

| | | |
|---|---|---|
| 7,332,159 B2 | 2/2008 | Labhasetwar et al. |
| 8,865,216 B2 | 10/2014 | Labhasetwar et al. |
| 9,138,416 B2 | 9/2015 | Labhasetwar et al. |
| 2006/0067925 A1 | 3/2006 | Labhasetwar et al. |

FOREIGN PATENT DOCUMENTS

WO 2014124142 A2 8/2014

OTHER PUBLICATIONS

Perera, 2009 PhD thesis, Cleveland State University, pp. 1-184.*
Carlyle et al. J Control Release, 2012, 162(3):561-567.*
Asahara, Takayuki, et al. "Local delivery of vascular endothelial growth factor accelerates reendothelialization and attenuates intimal hyperplasia in balloon-injured rat carotid artery." Circulation 91.11 (1995): 2793-2801.
Bowen, Paul. "Particle size distribution measurement from millimeters to nanometers and from rods to platelets." Journal of Dispersion Science and Technology 23.5 (2002): 631-662.
Cooke, MD, John P., and Victor J. Dzau, MD. "Nitric oxide synthase: role in the genesis of vascular disease." Annual review of medicine 48.1 (1997): 489-509.
Cooney, R., et al. "Effect of gene delivery of NOS isoforms on intimal hyperplasia and endothelial regeneration after balloon injury." Gene therapy 14.5 (2007): 396-404.
Davda, Jasmine, and Vinod Labhasetwar. "Sustained proangiogenic activity of vascular endothelial growth factor following encapsulation in nanoparticles." Journal of Biomedical Nanotechnology 1.1 (2005): 74-82.
Finn, Aloke V., et al. "Vascular responses to drug eluting stents importance of delayed healing." Arteriosclerosis, thrombosis, and vascular biology 27.7 (2007): 1500-1510.
Ignarro, Louis J., et al. "Role of the arginine-nitric oxide pathway in the regulation of vascular smooth muscle cell proliferation." Proceedings of the National Academy of Sciences 98.7 (2001): 4202-4208.
Iwakura, Atsushi, et al. "Estrogen-mediated, endothelial nitric oxide synthase—dependent mobilization of bone marrow—derived endothelial progenitor cells contributes to reendothelialization after arterial injury." Circulation 108.25 (2003): 3115-3121.
Janssens, Stefan, et al. "Human endothelial nitric oxide synthase gene transfer inhibits vascular smooth muscle cell proliferation and neointima formation after balloon injury in rats." Circulation 97.13 (1998): 1274-1281.
Joner, Michael, et al. "Site-specific targeting of nanoparticle prednisolone reduces in-stent restenosis in a rabbit model of established atheroma." Arteriosclerosis, thrombosis, and vascular biology 28.11 (2008): 1960-1966.
Kullo, Iftikhar J., et al. "Expression and function of recombinant endothelial NO synthase in coronary artery smooth muscle cells." Arteriosclerosis, thrombosis, and vascular biology 17.11 (1997): 2405-2412.

(Continued)

*Primary Examiner* — Bin Shen
(74) *Attorney, Agent, or Firm* — Tarolli, Sundheim, Covell & Tummino LLP

(57) ABSTRACT

A sustained-release composition for stimulating endothelial cell growth including a nitric oxide synthase within a nanoparticle comprising a biocompatible polymer is described. The sustained-release composition can be administered as part of a pharmaceutical composition, or can be coated on a medical device. The nitric oxide synthase-containing nanoparticles can be used in a method of inducing endothelium formation in a blood vessel.

24 Claims, 8 Drawing Sheets

(56) References Cited

OTHER PUBLICATIONS

Lindner, V., R. A. Majack, and M. A. Reidy. "Basic fibroblast growth factor stimulates endothelial regrowth and proliferation in denuded arteries." Journal of Clinical Investigation 85.6 (1990): 2004.

Napoli, Claudio, and Louis J. Ignarro. "Nitric oxide-releasing drugs." Annual review of pharmacology and toxicology 43.1 (2003): 97-123.

Panyam, Jayanth, et al. "Rapid endo-lysosomal escape of poly (DL-lactide-co-glycolide) nanoparticles: implications for drug and gene delivery." The FASEB Journal 16.10 (2002): 1217-1226.

Panyam, Jayanth, and Vinod Labhasetwar. "Dynamics of endocytosis and exocytosis of poly (D, L-lactide-co-glycolide) nanoparticles in vascular smooth muscle cells." Pharmaceutical research 20.2 (2003): 212-220.

Rome, Jonathan J., et al. "Anatomic barriers influence the distribution of in vivo gene transfer into the arterial wall. Modeling with microscopic tracer particles and verification with a recombinant adenoviral vector." Arteriosclerosis, Thrombosis, and Vascular Biology 14.1 (1994): 148-161.

Sah, Hongkee. "Stabilization of proteins against methylene chloride/water interface-induced denaturation and aggregation." Journal of controlled release 58.2 (1999): 143-151.

Sato, Jun'ichi, et al. "eNOS gene transfer to vascular smooth muscle cells inhibits cell proliferation via upregulation of p27 and p21 and not apoptosis." Cardiovascular research 47.4 (2000): 697-706.

Sharif, Faisal, et al. "Gene-eluting stents: adenovirus-mediated delivery of eNOS to the blood vessel wall accelerates re-endothelialization and inhibits restenosis." Molecular Therapy (2008).

Varenne, Olivier, et al. "Local adenovirus-mediated transfer of human endothelial nitric oxide synthase reduces luminal narrowing after coronary angioplasty in pigs." Circulation 98.9 (1998): 919-926.

Vasir, Jaspreet K., and Vinod Labhasetwar. "Quantification of the force of nanoparticle-cell membrane interactions and its influence on intracellular trafficking of nanoparticles." Biomaterials 29.31 (2008): 4244-4252.

Von Der Leyen, Heiko E., et al. "Gene therapy inhibiting neointimal vascular lesion: in vivo transfer of endothelial cell nitric oxide synthase gene." Proceedings of the National Academy of Sciences 92.4 (1995): 1137-1141.

Yu, Jun, Radu Daniel Rudic, and William C. Sessa. "Nitric oxide—releasing aspirin decreases vascular injury by reducing inflammation and promoting apoptosis." Laboratory investigation 82.7 (2002): 825-832.

PCT International Search Report and Written Opinion for PCT/US2016/027275, dated Jun. 21, 2016, pp. 1-13.

* cited by examiner

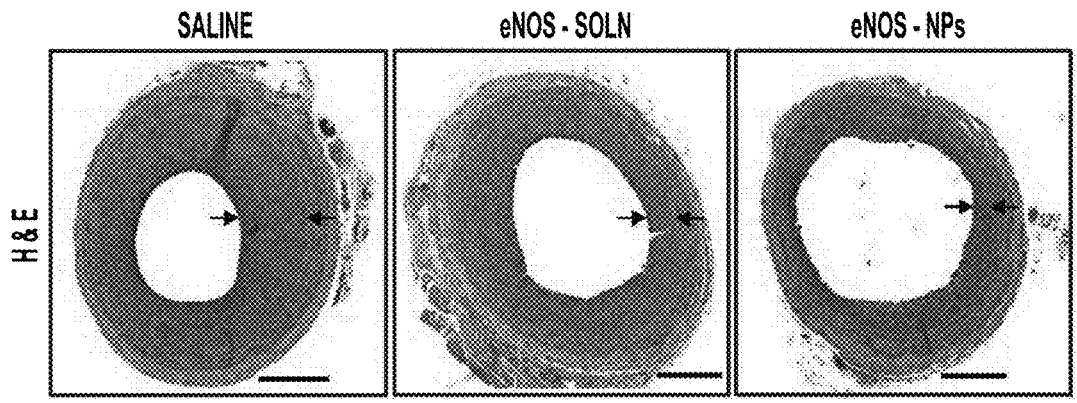
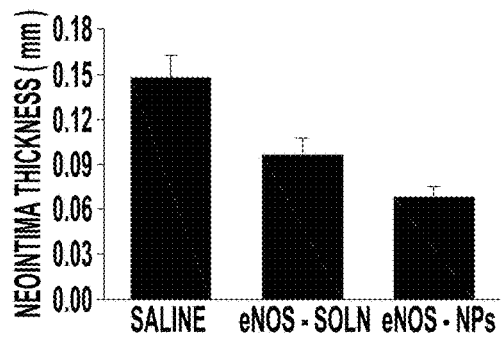
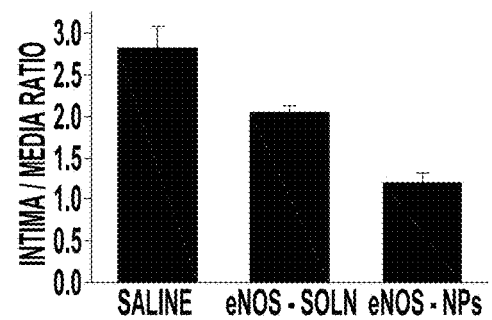
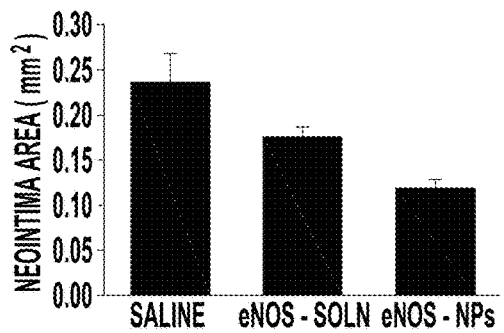
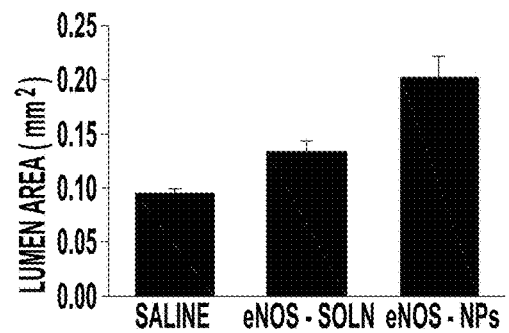

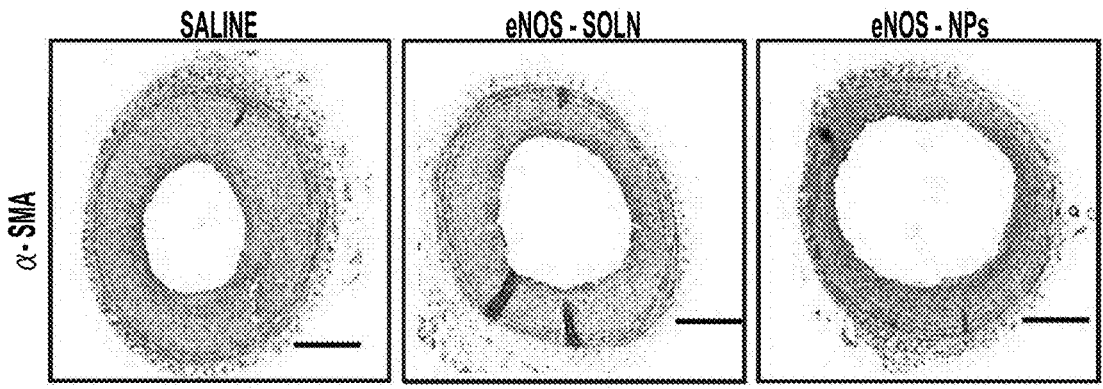
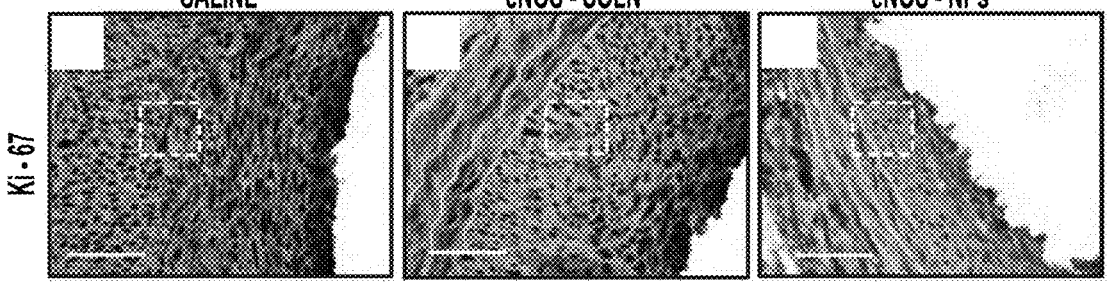
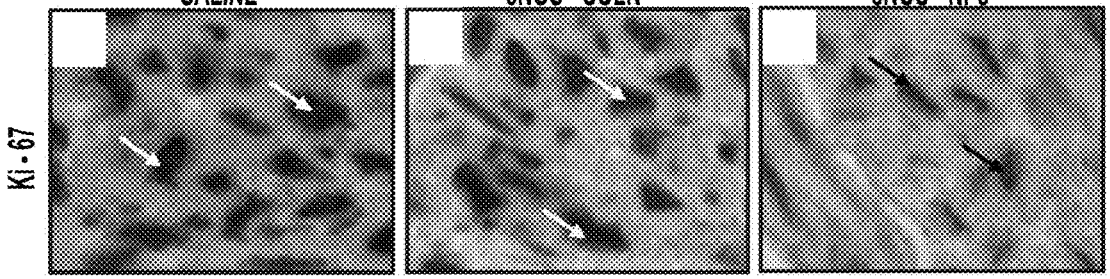
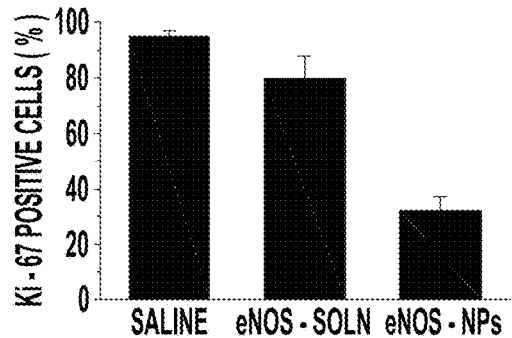

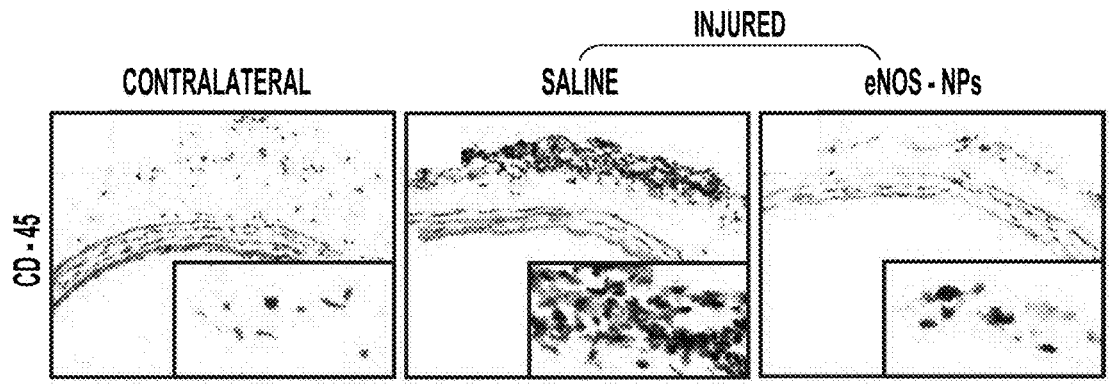
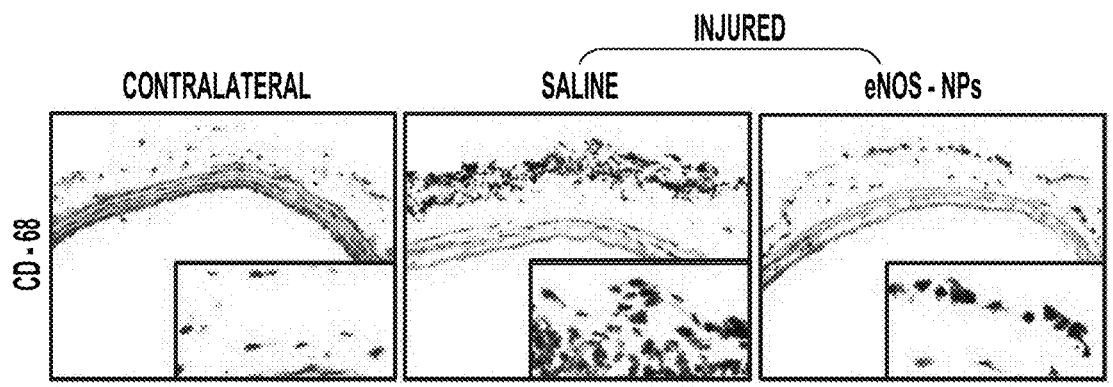
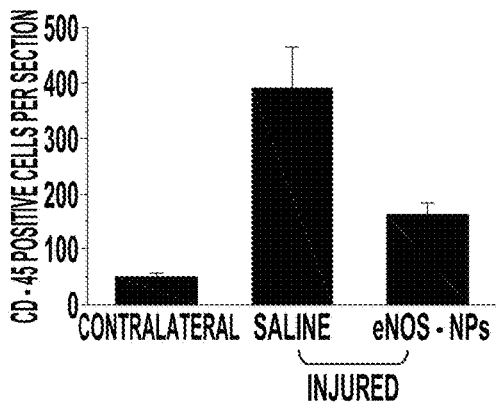
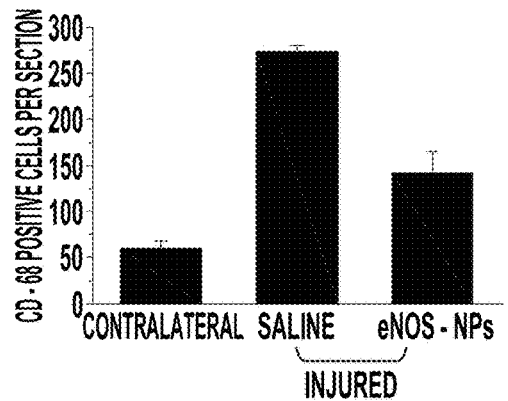
FIG. 4A   FIG. 4B   FIG. 4C
FIG. 4D   FIG. 4E   FIG. 4F
FIG. 4G   FIG. 4H

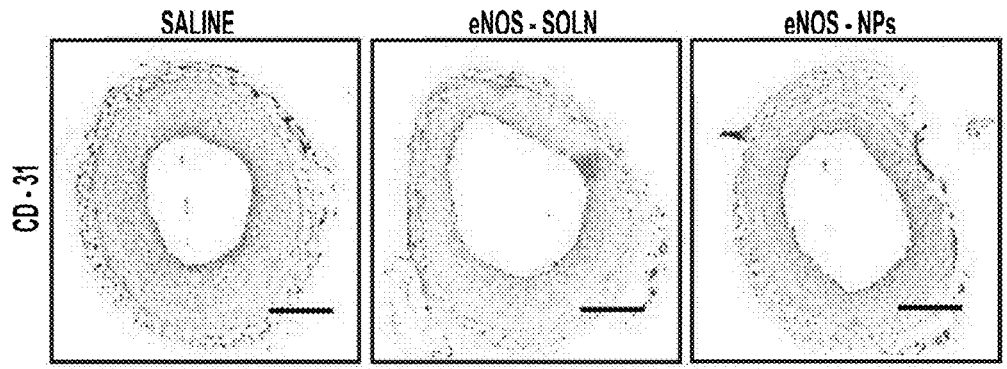
FIG. 5A  FIG. 5B  FIG. 5C
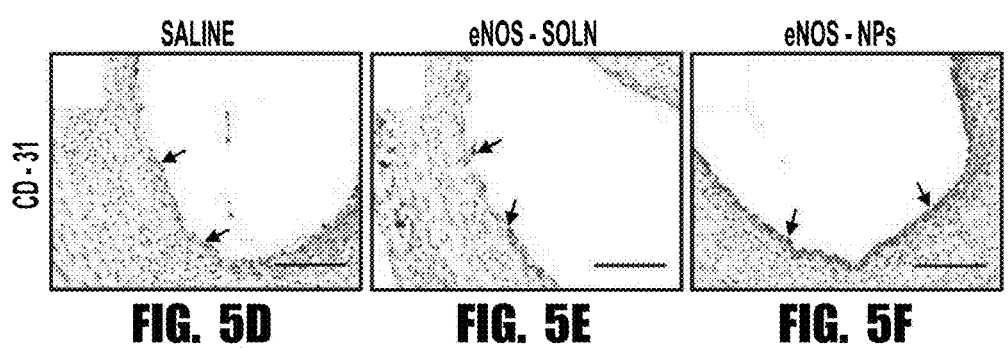
FIG. 5D  FIG. 5E  FIG. 5F
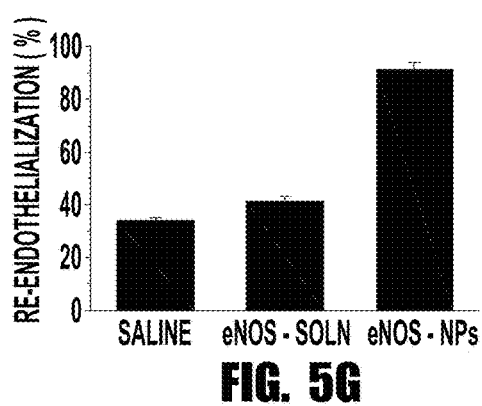
FIG. 5G
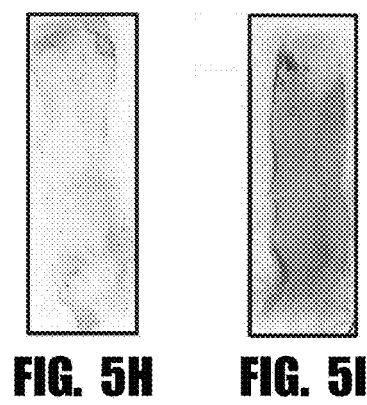
FIG. 5H  FIG. 5I

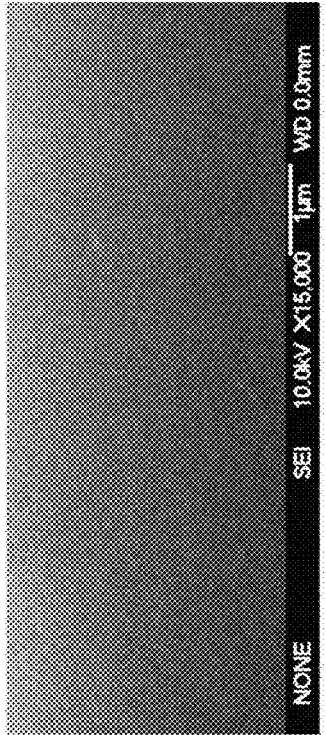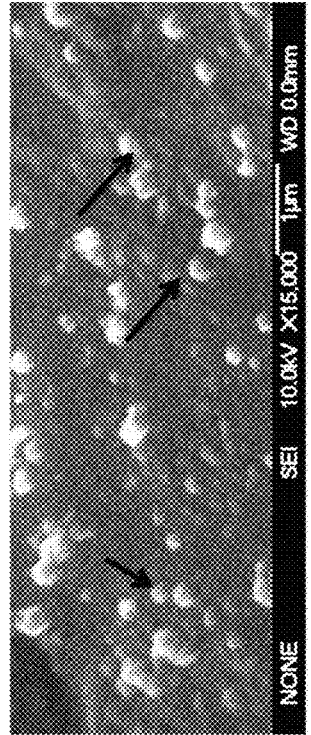
FIG. 8C SCANNING ELECTRON MICROSCOPY BEFORE COATING / COATED WITH NANO ARROWS SHOW NANOPARTICLES
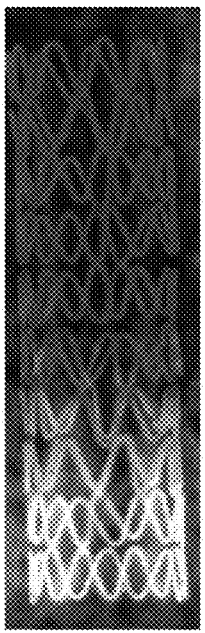
FIG. 8A OPTICAL IMAGING OF COATED STENT
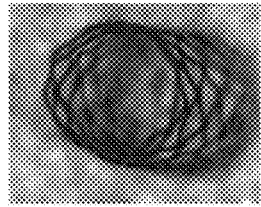
FIG. 8B TOP VIEW (SHOWS INSIDE OF STENT IS COATED)
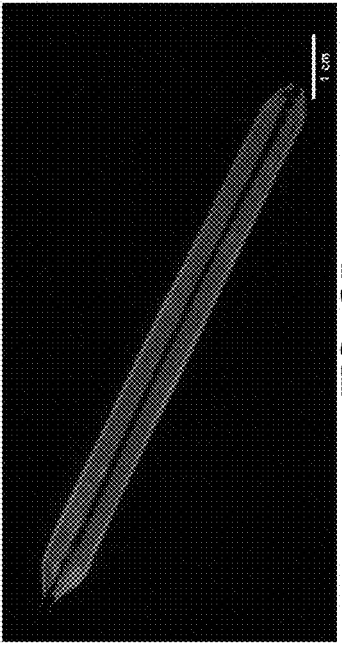
FIG. 8D NANOPARTICLE-COATED BALLOON BAR = 1 CM

NITRIC OXIDE SYNTHASE NANOPARTICLES FOR TREATMENT OF VASCULAR DISEASE

CROSS-REFERENCE TO RELATED APPLICATIONS

This application claims priority to U.S. Provisional Application Ser. No. 62/146,530, filed on Apr. 13, 2015, which is hereby incorporated by reference in its entirety.

BACKGROUND

Nitric oxide (NO) is one of the key regulatory molecules produced by endothelial nitric oxide synthase (eNOS, a constitutive isoform of nitric oxide synthase produced in endothelial cells), which plays a significant role in vascular homeostasis. NO counteracts pro-proliferating agents and growth factors, inhibits platelet aggregation, leukocyte adhesion, and maintains vascular smooth muscle cells (VSMCs) in a quiescent state. Vascular injury that leads to denudation of endothelium such as due to balloon inflation and/or stenting leads to the loss of endothelial cells producing vasoprotective eNOS, thereby leading to vascular deficiency of NO at the injured site. Studies have demonstrated an inverse relation between endothelial integrity and VSMC proliferation. Fishman et al., Lab Invest., 32:339-51 (1975).

Treatment modalities for vascular injury focus either on inhibiting VSMC proliferation or on promoting endothelial regeneration; however, an ideal anti-restenotic therapy should be able to achieve both of these effects as well as prevent constrictive remodeling of the artery. Endothelialization is key to the long-term patency of the artery, which is often delayed or inhibited in stented artery, and is implicated as one of the main causes of rebound of restenosis or fatal thrombosis. Finn et al., Arterioscler Thromb Vasc Biol., 27:1500-10 (2007). Thus, augmenting vasoprotective enzyme-eNOS and its "sustained" presence in the injured vessel wall is expected to maintain the vasoprotective functions of endothelium till re-endothelialization takes place via natural mechanisms. Though augmentation of NO levels in the injured vessel wall is a potential therapeutic strategy, its use is limited because of short half-life and high reactivity. The use of NO donors (e.g., organic nitrates, nitroglycerin, etc.) and NO-adducts with other pharmacological agents (e.g., NO-aspirin, NO-releasing statin derivatives etc.) is further limited due to the tolerance and potential hypotensive adverse effects. Napoli et al., Annu Rev Pharmacol Toxicol., 43:97-123 (2003). Localized eNOS gene transfer using HVJ-liposomes (von der Leyen et al., Proc Natl Acad Sci USA., 92:1137-41 (1995)) and adenovirus has shown to limit intimal hyperplasia (Janssens et al., Circulation., 97:1274-81 (1998); Varenne et al., Circulation, 98:919-26 (1998)); however, adenovirus carries the risk of inflammatory response and systemic expression of the transgene. Herz J, Gerard R D.; Proc Natl Acad Sci USA., 90:2812-6 (1993). Biodegradable nanoparticles (NPs) loaded with recombinant eNOS protein could potentially be a better alternative to eNOS gene transfer as NPs can release the encapsulated eNOS protein in active form for a prolonged period of time, irrespective of the functional nature of cellular machinery, which may be compromised under diseased conditions, thus influencing the efficiency of gene expression. Further, depending upon the response, the dose and duration of protein delivery in the target artery can be modulated with NPs, which is limited with gene therapy approaches.

SUMMARY

The inventors tested the hypothesis that the NP-mediated sustained delivery of recombinant eNOS protein in the target artery would augment NO synthesis that would inhibit the inflammatory process, thereby preventing the post-angioplasty hyperplasia and creating conditions conducive to facilitate the process of re-endothelialization. They developed surface functionalized biodegradable NPs formulated using poly-(DL-lactide-co-glycolide) (PLGA) polymer that result in efficient intracellular delivery of the encapsulated protein in active form. Vasir J K, Labhasetwar V., Biomaterials, 29:4244-52 (2008). The results demonstrated sustained localized delivery of eNOS protein in the target artery, providing vasoprotective activity of eNOS which resulted in inhibition of intimal hyperplasia and re-endothelialized the injured artery. The newly formed endothelium was shown to be functional.

In one aspect, the present invention provides a sustained-release composition for stimulating endothelial cell growth that includes a nitric oxide synthase within a nanoparticle comprising a biocompatible polymer. In some embodiments, the biocompatible polymer is a biodegradable polymer. In further embodiments, the nitric oxide synthase is endothelial nitric oxide synthase.

In another aspect, the present invention provides a method of inducing endothelium formation in a blood vessel that includes contacting the blood vessel with a nanoparticle comprising nitric oxide synthase within a biocompatible polymer. In some embodiments, the biocompatible polymer is a biodegradable polymer. In further embodiments, the nitric oxide synthase is endothelial nitric oxide synthase. In additional embodiments, the endothelium formation is induced in a subject to treat or prevent negative remodeling, thrombosis, vascular fibrosis, inflammation, platelet aggregation, hyperplasia, or restenosis of the blood vessel of the subject. In yet further embodiments, the subject has been diagnosed as having a renal or hepatic disease involving endothelial dysfunction.

In another aspect, the present invention provides an implantable or deliverable medical device coated with a sustained-release composition for stimulating endothelial cell growth, comprising a nitric oxide synthase within a nanoparticle comprising a biocompatible polymer. In some embodiments, the biocompatible polymer is a biodegradable polymer. In further embodiments, the nitric oxide synthase is endothelial nitric oxide synthase. In yet further embodiments, the implantable medical device is configured to fit within a blood vessel.

BRIEF DESCRIPTION OF THE FIGURES

FIG. 2A-FIG. 2G provide graphs and images showing the inhibition of intimal hyperplasia with eNOS-NPs in the rat carotid artery model of vascular injury at three weeks. (A-C) H & E stained arterial sections of animals treated with saline (A), eNOS protein solution (B), and with eNOS-NPs (C). Black arrows demarcate the neointima. Scale bar represents 200 nm. (D-G) Morphometric analysis of the arterial sections for neointima thickness (D), intima/media ratio (E), neointimal area (F), and lumen area (G). Quantitative data was derived from three equally spaced cross sections for artery from each animal in each group. *p<0.005 for treated (n=6) vs. saline (n=6) groups.

FIG. 3A-FIG. 3G provide graphs and images showing immunostaining for α-smooth muscle actin (α-SMA) for arteries from animals treated with saline (A), eNOS protein solution (B), and eNOS-NPs (C). Scale bar represents 200 nm. (D-J) Immunohistochemical analysis for Ki-67. Representative arterial sections stained for Ki-67, from the group: saline (D and G), eNOS protein solution (E and H), and eNOS-NPs (F and I). Brown nuclear staining represents Ki-67 while all nuclei were counterstained (blue) with hematoxylin. Scale bar represents 50 μm. Figure (G), Figure (H), and Figure (I) are magnified images of the insets outlined in Figure (D), Figure (E), and Figure (F), respectively. White arrows denote the Ki-67 positive nuclei and black arrows denote Ki-67 negative nuclei. The number of Ki-67 positive cells was calculated from nine serial sections per artery (n=6 rats per group). *p<0.005 for treated vs. saline group.

FIG. 4A-FIG. 4H provide graphs and images showing the Inhibition of inflammatory response with eNOS-NPs. (A-C) Immunostaining for CD-45 (marker for leukocytes) for uninjured contralateral arteries (A), injured arteries treated with saline (B), and eNOS-NPs (C). (D-F) Immunostaining for CD-68 (marker for macrophages) for uninjured contralateral arteries (D), injured arteries treated with saline (E), and eNOS-NPs (F). Brown staining represents CD-45 or CD-68 positive cells, while all nuclei were counterstained (blue) with hematoxylin. The number of CD-45 (G) and CD-68 (H) positive cells per section. The number of immunopositive cells were calculated from nine serial sections per artery (n=3 rats per group). *p<0.25 for treated vs. saline group.

FIG. 5A-FIG. 5I provide graphs and images showing re-endothelialization of denuded artery with eNOS-NPs. (A-F) Immunostaining for CD-31 (marker for endothelial cells). Representative arterial sections from the group: saline (A and D), eNOS protein solution (B and E), and eNOS-NPs (C and F) stained for CD-31 after 3 wk of vascular injury. Figure (D), Figure (E), and Figure (F) (scale bar=50 μm) are magnified images of Figure (A), Figure (B), and Figure (C) (scale bar=200 nm), respectively. Brown staining represents CD-31 positive cells, while all nuclei were counterstained (blue) with hematoxylin. Black arrows denote CD-31 positive cells. Re-endothelialization was calculated as the percentage of luminal surface covered by CD-31 positive cells (G) from three serial sections per artery (n=5 rats per group). *p<0.001 for treated vs. saline group. Representative arteries from rats injected with Evans blue dye: eNOS-NPs (H) show greater exclusion of dye than saline (I) indicating greater re-endothelialization.

FIG. 8A-FIG. 8D provides the images of a stent and balloon coated with protein-loaded NPs. For this, water-in-oil-water emulsion was sprayed onto a stent or balloon, and the coating was allowed to dry. NPs are formed in situ onto the stent or balloon surface. NPs contain a near-infrared dye which can be imaged using Maestro optical imaging system. (A) image showing coated and uncoated end of the stent; (B) top view of the coated stent showing that inside of the stent is coated with NPs; (C) Scanning electron microscopy of the coated stent showing NP deposits onto the surface of the stent; (D) image of the balloon coated with NPs.

DETAILED DESCRIPTION

Figure 1A:
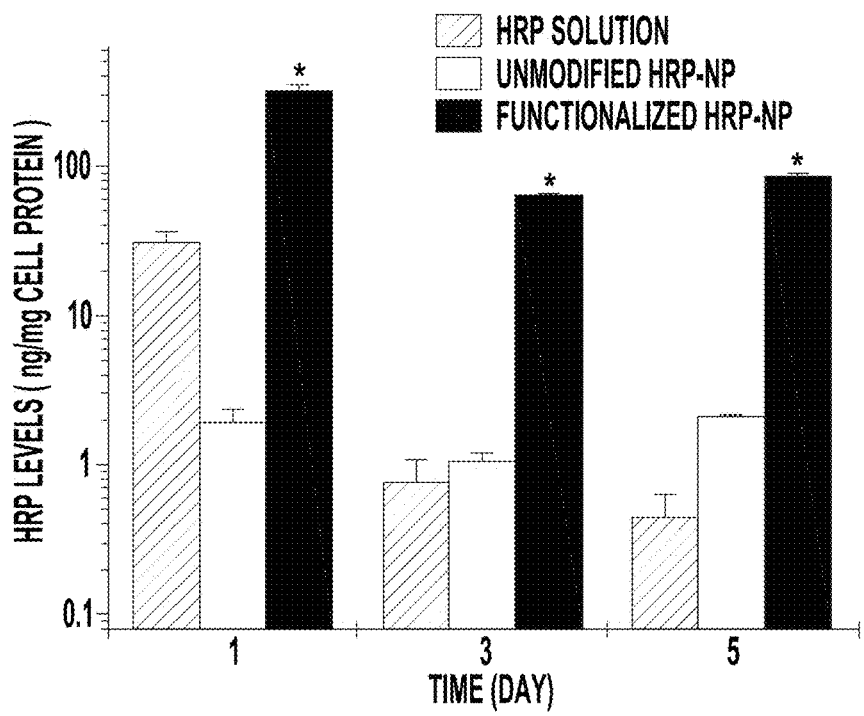
FIG. 1A and FIG. 1B provide graphs and images showing sustained cytoplasmic delivery of a model enzyme, horseradish peroxidase (HRP). Vascular smooth muscle cells were incubated with a 4-µg dose of HRP either in solution or encapsulated in NPs for 24 hr. Medium was changed after 24 hr and then on every alternate day. (A) After 1, 3 and 5 days, cells were lysed and their HRP levels were determined by activity assay of HRP. Amount of active HRP was normalized to the total cell protein. Data are presented as mean±standard deviation, n=6, (*) p<0.05. (B) After 1 and 5 days, cells were washed with PBS, fixed and incubated with DAB/Ni$^{2+}$ substrate to stain active HRP enzyme in (i, ii) cells treated with HRP solution, (iii, iv) HRP-loaded unmodified NPs, and (v, vi) HRP-loaded functionalized NPs.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, and other references mentioned herein are incorporated by reference in their entirety.

Definitions

As used in the description of the invention and the appended claims, the singular forms "a," "an," and "the" are intended to include the plural forms as well, unless the context clearly indicates otherwise. In addition, the recitations of numerical ranges by endpoints include all numbers subsumed within that range (e.g., 1 to 5 includes 1, 1.5, 2, 2.75, 3, 3.80, 4, 5, etc.).

"Treating", as used herein, means ameliorating the effects of, or delaying, halting or reversing the progress of a disease or disorder. The word encompasses reducing the severity of a symptom of a disease or disorder and/or the frequency of a symptom of a disease or disorder.

The language "effective amount" or "therapeutically effective amount" refers to a nontoxic but sufficient amount of the composition used in the practice of the invention that is effective to stimulate endothelial cell growth at the site of nanoparticle delivery. The desired treatment may be prophylactic and/or therapeutic. That result can be reduction and/or alleviation of the signs, symptoms, or causes of a disease or disorder, or any other desired alteration of a biological system. An appropriate therapeutic amount in any individual case may be determined by one of ordinary skill in the art using routine experimentation.

A "subject", as used therein, can be a human or non-human animal. Non-human animals include, for example, livestock and pets, such as ovine, bovine, porcine, canine, feline and murine mammals, as well as reptiles, birds and fish. Preferably, the subject is human.

"Pharmaceutically acceptable carrier" refers herein to a composition suitable for delivering an active pharmaceutical ingredient, such as the composition of the present invention, to a subject without excessive toxicity or other complications while maintaining the biological activity of the active pharmaceutical ingredient. Protein-stabilizing excipients, such as mannitol, sucrose, glucose, polysorbate-80 and phosphate buffers, polymers such as polyethylene glycol (PEG), polyvinyl alcohol (PVA), pluronics, are typically found in such carriers, although the carriers should not be construed as being limited only to these compounds.

The term "biodegradable" as used herein refers to a polymer that can be broken down by either chemical or physical process, upon interaction with the physiological environment subsequent to administration, and erodes or dissolves within a period of time, typically within days, weeks or months. A biodegradable material serves a temporary function in the body, and is then degraded or broken into components that are metabolizable or excretable.

"Biocompatible," as used herein, refers to any material that does not cause injury or death to the animal or induce an adverse reaction in an animal when placed in intimate contact with the animal's tissues. Adverse reactions include for example inflammation, infection, fibrotic tissue formation, cell death, or thrombosis. The terms "biocompatible" and "biocompatibility" when used herein are art-recognized and mean that the referent is neither itself toxic to a host (e.g., an animal or human), nor degrades (if it degrades) at a rate that produces byproducts (e.g., monomeric or oligomeric subunits or other byproducts) at toxic concentrations, does not cause prolonged inflammation or irritation, or does not induce more than a basal immune reaction in the host. It is not necessary that any subject composition have a purity of 100% to be deemed biocompatible. Hence, a subject composition may comprise 99%, 98%, 97%, 96%, 95%, 90% 85%, 80%, 75% or even less of biocompatible agents, e.g., including polymers and other materials and excipients described herein, and still be biocompatible.

Nanoparticles Including Nitric Oxide Synthase

In one aspect, the present invention provides a sustained-release composition for stimulating endothelial cell growth, comprising a nitric oxide synthase within a nanoparticle comprising a biocompatible polymer. A variety of release kinetics are contemplated for the sustained release of the nitric oxide synthase from the nanoparticle, including bi- or multi-phase release (such as an initial fast release followed by a slower subsequent release phase). For example, the release may include dissociation of the nitric oxide synthase from the nanoparticle rapidly within seconds or minutes followed by further sustained release over a period of at least 2, 4, 6, 8 or more hours to weeks and months. Such release kinetics may be advantageous in certain circumstances, e.g. where sustained action is desired, in comparison with, e.g., an injection of free enzyme.

The nanoparticles of the present invention are useful for stimulating endothelial cell growth. The endothelium is the thin layer of squamous cells that lines the interior surface of blood vessels and lymphatic vessels, forming an interface between circulating blood or lymph in the lumen and the rest of the vessel wall. The cells that form the endothelium are called endothelial cells. Endothelial cells in direct contact with blood are called vascular endothelial cells, whereas those in direct contact with lymph are known as lymphatic endothelial cells. If the endothelium is damaged as a result of, for example, disease or surgical intervention, it is important to repair the endothelium to allow the blood and/or lymphatic vessels to return to normal function. The inventors have shown that sustained release of nitric oxide synthase from the nanoparticles of the present invention can stimulate endothelial cell growth, thereby repairing the endothelium, a process also referred to herein as re-endothelialization. Stimulating endothelial cell growth refers to increasing the rate of endothelial cell growth. The present invention can cause endothelial cell growth to occur where there previously was no endothelial cell growth, or it may increase an existing rate of endothelial cell growth. For example, the present invention can increase endothelial cell growth by 5%, 10%, 15%, 20%, 25%, 30%, 35%, 40%, 50%, 60%, 70%, 80%, 90%, 100%, or more than 100%. Re-endothelialization could also occur due to circulating progenitor cells anchoring at the injured artery and eNOS promoting their differentiation to endothelial cells and formation of endothelium.

Nitric oxide synthases (EC 1.14.13.39) (NOSs) are a family of enzymes catalyzing the production of nitric oxide (NO) from L-arginine. Nitric oxide is mediated in mammals by the calcium-calmodulin controlled isoenzymes eNOS (endothelial NOS) and nNOS (neuronal NOS). The amount of nitric oxide synthase delivered by each nanoparticle can vary depending on the size of the nanoparticles and the desired dosage. In some embodiments, the weight/weight (w/w) percent of the nitric oxide synthase in the nanoparticles is about 3%. In other embodiments, the w/w percent of the nitric oxide synthase nanoparticles is about 1-10%.

The present invention includes nanoparticles delivering any type of nitric oxide synthase, but in some embodiments, the nitric oxide synthase is endothelial nitric oxide synthase (eNOS). In mammals, the endothelial isoform is the primary signal generator in the control of vascular tone, insulin secretion, and airway tone, is involved in regulation of cardiac function and angiogenesis (growth of new blood vessels). NO produced by eNOS has been shown to be a vasodilator identical to the endothelium-derived relaxing factor produced in response to shear from increased blood flow in arteries. This dilates blood vessels by relaxing smooth muscle in their linings. eNOS is the primary controller of smooth muscle tone. NO activates guanylate cyclase, which induces smooth muscle relaxation Preservation of endothelial function is important in maintaining normal kidney function. A key role of the endothelium is to produce nitric oxide (NO), which is catalyzed by endothelial NO synthase (eNOS) and induce a vasodilator that helps maintain endothelial cell integrity with antithrombotic properties.

The nitric oxide synthase can be included in the nanoparticles in various different ways. For example, the nitric oxide synthase can be dispersed within the nanoparticle, or it can be encapsulated within the nanoparticle. In some embodiments, the nitric oxide synthase is substantially evenly dispersed within the nanoparticle. Nitric oxide synthase can be conjugated to nanoparticle surface, or it can be a combination of the surface associated and encapsulated in nanoparticle core.

Nanoparticles, as the term is used herein, are particles having a matrix-type structure with a size of 1000 nanometers or less. The nanoparticles are generally spherical structures. In some embodiments, the nanoparticles have a size of 500 nanometers or less. In some embodiments, the particles have a diameter from 10 nanometers to 1000 nanometers. In other embodiments, the particles have a diameter from 10 nanometers to 500 nanometers. In further embodiments, the particles have a diameter from 10 to 300 nanometers, while in yet further embodiments the particles have a diameter from 50 to 300 nanometers. The diameter of the nanoparticles refers to their mean hydrodynamic diameter. The hydrodynamic diameter can be readily determined using dynamic light scattering (DLS).

The nanoparticles of the invention can be prepared using a wide variety of different types of polymers. Preferably, the nanoparticle comprises one or more biocompatible polymers. Examples of biocompatible polymers include natural or synthetic polymers such as polystyrene, polylactic acid, polyketal, butadiene styrene, styreneacrylic-vinyl terpolymer, polymethylmethacrylate, polyethylmethacrylate, polyalkylcyanoacrylate, styrene-maleic anhydride copolymer, polyvinyl acetate, polyvinylpyridine, polydivinylbenzene, polybutyleneterephthalate, acrylonitrile, vinylchloride-acrylates, polycaprolactone, poly(alkyl cyanoacrylates), poly(lactic-co-glycolic acid), and the like.

In further embodiments, the nanoparticle comprises one or more biodegradable polymers. Use of biodegradable polymers provides the advantages of using nanoparticles that will eventually disintegrate, which facilitates release of the nitric oxide synthase and elimination of the nanoparticles in vivo. However, nitric oxide synthase can also be released from the matrix of non-biodegradable polymers as a result of gradual efflux from channels within the polymer matrix, including those formed by soluble materials included in the polymer matrix.

Examples of biodegradable polymers include polylactide polymers include poly(D,L-lactide)s; poly(lactide-co-glycolide) (PLGA) copolymers; polyglycolide (PGA) and polydioxanone; caprolactone polymers; chitosan; hydroxybutyric acids; polyanhydrides and polyesters; polyphosphazenes; and polyphosphoesters. A preferred biodegradable polymer for use in the nanoparticles is poly-(D,L-lactide-co-glycolide).

Functionalized poly(D,L-lactide)s can also be used as biodegradable polymers in the nanoparticles of the invention. Examples of functionalized poly(D,L-lactide)s include poly(L-lactide), acrylate terminated; poly(L-lactide), amine terminated; poly(L-lactide), azide terminated; poly(L-lactide), 2-bromoisobutyryl terminated; poly(L-lactide), 2-bromoisobutyryl terminated; poly(L-lactide) 4-cyano-4-[(dodecylsulfanylthiocarbonyl)sulfanyl]pentonate; poly(L-lactide) N-2-hydroxyethylmaleimide terminated; poly(L-lactide) 2-hydroxyethyl, methacrylate terminated; poly(L-lactide), propargyl terminated; poly(L-lactide), thiol terminated;

Other biodegradable polymers that can be used in the nanoparticles include AB diblock copolymers such as poly(ethylene glycol) methyl ether-block-poly(D,L-lactide); poly(ethylene glycol) methyl ether-block-poly(lactide-co-glycolide) PEG; poly(ethylene glycol)-block-poly(ε-caprolactone) methyl ether PEG; and polypyrrole-block-poly(caprolactone). Further biodegradable polymers include ABA triblock copolymers such as polylactide-block-poly(ethylene glycol)-block-polylactide PLA; poly(lactide-co-glycolide)-block-poly(ethylene glycol)-block-poly(lactide-co-glycolide); poly(lactide-co-caprolactone)-block-poly(ethylene glycol)-block-poly(lactide-co-caprolactone); polycaprolactone-block-polytetrahydrofuran-block-polycaprolactone; and polyglycolide-block-poly(ethylene glycol)-block-polyglycolide PEG.

Another biodegradable polymer that can be used in some embodiments of the invention is an N-alkylacrylamide copolymer. N-alkylacrylamide is a hydrophobic monomer having an alkyl group of $C_3$ to $C_6$. For example, in some embodiments, the biodegradable polymer is a copolymer of an N-alkylacrylamide, a vinyl monomer, and a polyethylene glycol (PEG) conjugate. However, in some embodiments, the biodegradable polymer is any of the biodegradable polymers described herein other than a copolymer of an N-alkylacrylamide, a vinyl monomer, and a PEG conjugate. Use of nanoparticles comprising biodegradable polymers a copolymer of an N-alkylacrylamide, a vinyl monomer, and a PEG conjugate are described in U.S. Pat. No. 9,138,416, the disclosure of which is incorporated herein by reference.

Biodegradable polymers also include various natural polymers. Examples of natural polymers include polypeptides including those modified non-peptide components, such as saccharide chains and lipids; nucleotides; sugar-based biopolymers such as polysaccharides; cellulose; carbohydrates and starches; dextrans; lignins; polyamino acids; adhesion proteins; lipids and phospholipids (e.g., phosphorylcholine).

In some embodiments, the nanoparticle comprises a modified nanoparticle. Modified nanoparticles, also referred to as functionalized nanoparticles, are described in U.S. Pat. No. 8,865,216, the disclosure of which is incorporated herein by reference. Modified nanoparticles comprise a biocompatible polymer having a net negative charge at neutral pH, at least one charge modulator that is effective to reverse the surface charge from negative to positive in an acidic environment, and optionally an amphiphilic emulsifier. Modified nanoparticles are prepared using the combination of poly vinyl alcohol (or other amphiphilic emulsifier) with poly-L-lysine (or other charge modulator) are referred to herein as modified or surface modified nanoparticles. Generally speaking, surface modification of nanoparticles produces a significant increase in the cellular uptake, as compared to unmodified nanoparticles.

The nanoparticles of the invention can include compounds in addition to the nitric oxide synthase. For example, the nanoparticles can include an additional protein such as albumin within the nanoparticle. The presence of an additional protein (e.g., albumin) can be useful for facilitating release of eNOS from the nanoparticle by acting as a bulking agent. The presence of an additional protein (e.g., albumin) can also serve to protect eNOS from interfacial inactivation by contact with the organic/aqueous interface during preparation of the eNOS-containing nanoparticles. In other embodiments, the nanoparticle includes one or more cofactors to assist nitric oxide synthase formation of nitric oxide. NOSs are unusual in that they generally require five cofactors. Accordingly, in some embodiments, the composition further comprises one or more nitric oxide synthase cofactors. Nitric oxide synthase cofactors include tetrahydrobiopterin ($BH_4$), guanosine triphosphate (GTP), cyclohydrolase, and L-arginine. In certain disease conditions (e.g., diabetes), tissue deficiency of these co-factors is responsible for reduced production of nitric oxide.

In some embodiments, an additional therapeutic agent is administered to the subject. The additional therapeutic agent can be administered concurrent with or subsequent to the administration of the nitric oxide synthase-containing nanoparticles. The therapeutic agent can be included in the nanoparticles, or it can be administered separately. In some embodiments, the additional therapeutic agent is nitric oxide synthase that is administered in combination with the nitric oxide synthase-containing nanoparticles but using a different method of delivery. For example, nitric oxide synthase can be co-administered with nitric oxide synthase-containing nanoparticles in a pharmaceutically acceptable solution or in a gel.

Therapeutic agents that can be utilized within the present invention include cardiovascular agents such as antihypertensive agents; adrenergic blockers and stimulators (e.g., doxazosin, guanadrel, guanethidine, pheoxybenzamine, terazosin, clonidine, guanabenz); alpha-/beta-adrenergic blockers (e.g., labetalol); angiotensin converting enzyme (ACE) inhibitors (e.g., benazepril, catopril, lisinopril, ramipril); ACE-receptor antagonists (e.g., losartan); beta blockers (e.g., acebutolol, atenolol, carteolol, pindolol, propranolol, penbatolol, nadolol); calcium channel blockers (e.g., amiloride, bepridil, nifedipine, verapamil, nimodipine); antiarrythmics, groups I-IV (e.g., bretylium, lidocaine, mexiletine, quinidine, propranolol, verapamil, diltiazem, trichlormethiazide, metoprolol tartrate, carteolol hydrochloride); and miscellaneous antiarrythmics and cardiotonics (e.g., adenosine, digoxin, caffeine, dopamine hydrochloride, digitalis).

Other therapeutic agents that can be used in accord with the present invention include anti-inflammatory agents. Representative examples of such agents include nonsteroidal agents (NSAIDS) such as salicylates, diclofenac, diflunisal, flurbiprofen, ibuprofen, indomethacin, mefenamic acid, nabumetone, naproxen, piroxicam, ketoprofen, ketorolac, sulindac, tolmetin. Other anti-inflammatory drugs include steroidal agents such as beclomethasone, betamethasone, cortisone, dexamethasone, fluocinolone, flunisolide, hydorcortisone, prednisolone, and prednisone. Immunosuppressive agents are also contemplated (e.g., adenocorticosteroids, cyclosporin).

Other therapeutic agents include agents that inhibit tissue damage. Representative examples of such agents include antioxidants such as superoxide dismutase, catalase, glutathione, Vitamin E; immune modulators (e.g., lymphokines, monokines, interferon α and β); and growth regulators (e.g., IL-2, tumor necrosis factor, epithelial growth factor, vascular endothelial growth factor, fibroblast growth factor, transforming growth factor-beta, somatrem, fibronectin, GM-CSF, CSF, platelet-derived growth factor, somatotropin, rG-CSF, epidermal growth factor, IGF-1).

In further embodiments, the therapeutic agent is an anti-restenotic agent, or anti-apoptic agent. Examples of anti-restenotic agent include rapamycin (i.e., sirolimus) or a derivative or analog thereof, e.g., everolimus or tacrolimus. Examples of anti-apoptic agents include Galectin-3; (−)deprenyl; monoamine oxidase inhibitors (MAO-I) such as selegiline and rasagiline; Rapamycin; or quercetin; Paclitaxel Inducing Endothelium Formation Using Nitric Oxide Synthase Nanoparticles Another aspect of the present invention provides a method of inducing endothelium formation in a blood vessel. The method includes contacting the blood vessel with a nanoparticle comprising nitric oxide synthase within a biocompatible polymer. The nitric oxide synthase-containing nanoparticle can include any of the polymers and other compounds described for the nanoparticles of the invention. Inducing endothelium formation involves the stimulation of endothelial cell growth, in which the growing endothelial cells repair or increase the diameter of the endothelial layer within a blood vessel. Blood vessels are the part of the circulatory system that transport blood throughout the body. Blood vessels include arteries, which carry the blood away from the heart; capillaries, which enable the actual exchange of water and chemicals between the blood and the tissues; and the veins, which carry blood from the capillaries back toward the heart. Examples of blood vessels include coronary, femoral, renal, hepatic, and cerebral arteries.

In some embodiments, endothelium formation in a blood vessel is induced in a subject to treat or prevent a disease or disorder in which the endothelium plays a role. In particular, methods of the invention can be directed to inducing endothelium formation to increase or replace endothelium that has been damaged or lost as a result of the disease or disorder. Examples of diseases or disorders in which the endothelium plays a role include negative remodeling, thrombosis, vascular fibrosis, inflammation, platelet aggregation, hyperplasia, and restenosis of the blood vessel of a subject. In other embodiments, the method is used to treat a subject that has been diagnosed as having diabetic nephrophathy, while in further embodiments the method is used to treat a subject that has been diagnosed as having a renal or hepatic disease involving endothelial dysfunction. In some embodiments, the nanoparticles are used to treat heart failure, as NO deficiency causes pulmonary endothelial dysfunction-considered as the cause of heart failure. In other embodiments, the nanoparticles are used to treat liver cirrhosis. In liver cirrhosis intrahepatic endothelial dysfunction is caused by eNOS and other co-factor deficiency (L-arginine and tetrahydrobiopterin, $BH_4$) that is responsible for production of NO.

Coated Medical Devices

Another aspect of the invention provides an implantable or deliverable medical device coated with a sustained-release composition for stimulating endothelial cell growth, comprising a nitric oxide synthase within a nanoparticle comprising a biocompatible polymer. The nanoparticle can include any of the compounds, and use any of the polymers, described herein for the nanoparticles of the invention. In some embodiments, the implantable or deliverable medical device is configured to fit within a blood vessel.

A wide variety of medical devices are known to those skilled in the art that can be coated with a composition comprising the nitric oxide synthase-containing nanoparticles of the invention. Examples of medical devices include stents, drug eluting stents; balloons, double balloon catheters; infusion catheters; vascular grafts (synthetic or biological); implanted blood access devices for hemodialysis; percutaneous medical devices; guide wires; artificial hearts, heart valves, venous valves, shunts), endovascular coils used in aneurism; pacemaker leads; intravascular and cardiovascular mesh; blood filters; transducers; blood tubing connectors; sutures; clips for coronary artery bypass graft; fistula; implantable cardioverter defibrillators; metal screws, pins, plates, and rods; intravenous catheter cannula; guide catheters; implantable electrodes, sensors, cardiac/cerebral/pulmonary shunts; pouches; wound closure dressing/glue; occluder balloons, and intravenous extension tubing. In some embodiments, the nanoparticles are used to coat non-implantable medical devices such as surgical tools. Preferred examples of implantable medical devices include vascular grafts, stents, and balloon catheters.

The medical devices include a wide variety of biocompatible medical materials. For example, the medical devices can include biocompatible ceramics such as aluminum oxide, calcium oxide, hydroxyapatite, and zirconium(IV) oxide. The medical devices can also include biocompatible metals such as titanium or stainless steel. A wide variety of biocompatible polymers can also be used. Examples of biocompatible polymers include polyacrylics, polyamides, polyimides, polycarbonates, polydienes, polyesters, polyethers, polyfluorocarbons, polyolefins, polystyrenes, poly vinyl acetals, polyvinyl and vinylidene chlorides, polyvinyl esters, polyvinyl ethers and ketones, polyvinylpyridine, and polyvinypyrrolidone polymers.

A variety of methods can be used to coat the nanoparticles onto the surface of the implantable medical device. Examples of coating methods include spray coating, deep coating, and jet spraying a dry/dispersion of nanoparticles. An early step in coating the surface of an implantable medical device can be making the surface micro/nanoporous to facilitate embedding the nanoparticles on the surface. A cross-linking agent can be used to help attached the nanoparticles to the surface of the medical device. Examples of suitable cross-linking agents include di(ethylene glycol) dimethacrylate, divinylbenzene, and tetraethylene glycol dimethyl ether.

A variety of other specific steps may be involved in coating an implantable medical device with the nanoparticles. For example, it is sometimes advantageous to first coat the medical device with hydrogel, and then coat it with the nanoparticles. Alternately, the nanoparticles can be mixed with the hydrogel first and then coated onto the implantable medical device. Other methods of coating include surface activation first with cross-linking agent and then coating with nanoparticles; layer coating-first a drug-loaded polymer layer and then the nanoparticles; mixing of the nanoparticles with polymer matrix (in case of biodegradable stents); in situ formation on nitric oxide synthase-containing nanoparticles on the surface of the medical device; coating with lipids/phospholipids and then nanoparticles; mixing lipids/phospholipids with nanoparticles and then using the combination for coating; and first coating with polyionic or ionic agents (polymers, amino acids, lipids, etc.) and then with nanoparticles, in situ formation of nanoparticles onto the medical device where nanoparticles are formed onto medical device, iontophoretic deposition of nanoparticles, layer-by-layer deposition, with combination of drug and nanoparticles. In some embodiments, it may also be helpful to form a scaffold onto a surface and then embed nanoparticles in the scaffold.

Formulation and Administration

The nanoparticles are often provided on the surface of a medical device such as an implantable medical device. For example, the nanoparticles can be provided on coated stents or other devices as listed above; such as coated balloons (e.g., infusion balloon; double balloon catheter for localized infusion). Other forms of nanoparticle delivery include use of a transluminal local drug delivery device or transendocardial delivery system; intravascular or intra-arterial, cerebrovascular delivery using infusion catheters; periadventitial delivery; perivascular delivery; direct injection into arterial wall; intravenous/intra-arterial injection; intravenous/intra-arterial infusion; localized tissue injection near affected blood vessel; microneedle patches; and administration using a microneedle injection balloon In some embodiments, the nanoparticles are administered as part of a pharmaceutical composition. For example, in some embodiments, a nanoparticle of the invention maybe combined with a pharmaceutically acceptable vehicle or carrier to provide a pharmaceutical composition. The nanoparticles may be present in a pharmaceutical composition in an amount from 0.001 to 99.9 wt %, more preferably from about 0.01 to 99 wt %, and even more preferably from 0.1 to 95 wt %. For instance, in embodiments where the nanoparticles are administration by injection (e.g., intraperitoneally, intravenously, subcutaneously, intramuscularly, etc.), the compositions are preferably combined with pharmaceutically acceptable vehicles such as saline, Ringer's solution, dextrose solution, and the like.

The compositions for administration will commonly comprise a suspension of the nanoparticles in a pharmaceutically acceptable carrier, preferably an aqueous carrier, which is selected so as not to affect the biological activity of the combination. Examples of such carriers are distilled water, physiological phosphate-buffered saline, Ringer's solutions, dextrose solution, and Hank's solution. These suspensions are sterile and generally free of undesirable matter. These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

Single or multiple administrations of the compositions may be administered depending on the dosage and frequency as required and tolerated by the subject. In any event, the administration regime should provide a sufficient quantity of the composition of this invention to effectively treat the subject. The formulated nanoparticles can be administered as a single dose or in multiple doses.

One of skill in the art will recognize that the amount of the nanoparticles in the formulations can vary widely, and will be selected primarily based on fluid volumes, viscosities, body weight and the like in accordance with the particular mode of administration selected and the subject's needs. In one embodiment, the amount of nanoparticle administered is between about 0.25 mol/kg and about 3 mol/kg equivalent of enzyme. In another embodiment, the amount of nanoparticle administered is between about 0.5 mol/kg and about 1.5 mol/kg equivalent of. In yet another embodiment, the amount of nanoparticle administered is about 1 mol/kg equivalent of enzymes. In still another embodiment, the amount of nanoparticle administered is between about 0.1 g/kg and about 0.5 g/kg.

The following examples are included for purposes of illustration and are not intended to limit the scope of the invention.

EXAMPLES

Example 1: Nanoparticle-Mediated eNOS Protein Therapy to Inhibit Post-Angioplasty Hyperplasia in Rat Model of Vascular Injury Endothelium is responsible for producing the vasoprotective enzyme, endothelial nitric oxide synthase (eNOS), which produces nitric oxide (NO). NO regulates vascular tone, prevents thrombogenicity, and maintains vascular smooth muscle cells (VSMCs) in a quiescent state. Vascular interventions such as balloon angioplasty or stenting result in denudation of endothelium, causing vascular deficiency of NO that leads to migration and proliferation of VSMCs, thus causing intimal hyperplasia. The inventors tested the hypothesis that localized and sustained delivery of recombinant eNOS protein would augment NO synthesis in the target artery and thereby inhibit the post-angioplasty hyperplasia. Functionalized biodegradable nanoparticles, designed to enhance cellular uptake and arterial localization, and release the encapsulated protein in active form, were used to deliver eNOS protein intraluminally in a rat carotid artery model of vascular injury. The results demonstrated (i) sustained eNOS protein activity in the target artery, extending over three weeks, (ii) inhibition of hyperplasia (Intima to Media ratio, I/M=1.15±0.10 vs. 2.81±0.27 (control); $p<0.005$), and (iii) re-endothelialization of the injured artery (endothelium coverage; 91% vs. 34% (control); $p<0.001$). eNOS protein delivery inhibited the recruitment of leukocytes and infiltration of macrophages in the injured artery, thus preventing the inflammatory process which, in turn, could have created conditions conducive to facilitate re-endothelialization. This is the first work demonstrating the efficacy of vascular delivery of eNOS protein to restore the vasoprotective functions of NO.

Materials and Methods

Formulation and Characterization of eNOS Protein-Loaded NPs

NPs containing eNOS protein were formulated with PLGA polymer using a double emulsion solvent evaporation technique. Vasir J K, Labhasetwar V., Biomaterials, 29:4244-52 (2008). In brief, an aqueous solution of eNOS protein (1 mg) and rat serum albumin (RSA) (10 mg) in 250 µl of 50 mmol/L triethanolamine buffer (pH 7.5, containing 0.5 mmol/L EDTA) was emulsified into a polymer solution (27 mg PLGA polymer and 3 mg tartaric acid dimethyl ester [DMT] in 1 ml of chloroform) using a probe sonicator (55 W for 1 min in an ice bath). RSA was used to stabilize eNOS protein from interfacial inactivation (Sah H., J Control Release, 58:143-51 (1999)), and DMT to facilitate the release of the encapsulated protein from NPs. Labhasetwar V, Reddy M K., U.S. Pat. No. 7,332,159. This primary water-in-oil emulsion was further emulsified into 8 ml of an aqueous solution containing polyvinyl alcohol (PVA; 2.0% w/v) and poly-L-lysine (PLL; 0.5% w/v), using the probe sonicator as above for 3 min to form a double water-in-oil-in-water emulsion. The double emulsion was continuously stirred overnight to evaporate chloroform; NPs with encapsulated protein were recovered by ultracentrifugation and were subsequently lyophilized. NPs were characterized for particle size, zeta potential, and protein loading.

Balloon Injury and Local Delivery of eNOS-NPs in Rat Model

All animal experiments were performed according to the animal welfare policy of the American Heart Association and the Institutional Animal Care and Use Committee of the Lerner Research Institute, Cleveland Clinic. Male Sprague Dawley rats (380 to 400 g, Charles River Laboratories, Wilmington, Mass.) underwent a carotid artery balloon angioplasty procedure using a 2F Fogarty balloon catheter (Edwards Life Sciences, Irvine, Calif.). A PE 10 catheter was used to infuse a suspension of NPs (210 µl saline containing 3 mg of eNOS-NPs which is equivalent to 72 µg of eNOS protein) into the injured carotid artery over 5 min at 2 atm of pressure (three infusions of 70 µl each, with a 1 min period between infusions). The above dose of eNOS protein was based on the results of our preliminary studies with two doses of eNOS protein (36 and 72 µg) loaded NPs. Animals were randomly divided into three groups (n=6 animals per group), and received an infusion of either (i) eNOS protein solution, (ii) a suspension of eNOS-NPs, or (iii) saline (control). Animals treated with void-NPs show the similar extent of hyperplasia as saline control; hence saline was used as a control in all the experiments.

Immunohistochemistry

Animals were euthanized at 1 day for evaluation of leukocyte/macrophage infiltration at the injury site, at 7 and 21 days post-angioplasty for evaluation of proliferating cells and re-endothelialization. Serial arterials sections were immunostained using different antibodies: mouse monoclonal anti-CD-45 antibody for leukocytes, anti-rat CD-68 antibody for macrophages, rabbit polyclonal anti-Ki-67 antibody for proliferating cells, rabbit polyclonal anti-smooth muscle actin antibody for VSMCs, rabbit polyclonal anti-CD-31 antibody for endothelial cells, and rabbit polyclonal anti-eNOS antibody for eNOS.

Re-Endothelialization

Re-endothelialization was calculated as the percentage of luminal surface covered by CD-31 positive cells three weeks after angioplasty. Additionally, in a separate experiment, the extent of Evan's blue dye extravasation (blue staining) was used as an index for endothelial cell lining integrity. Thirty minutes before euthanasia, rats received an intravenous injection of the dye solution (0.5 mL of 0.5% solution). Carotid arteries were harvested following transcardial perfusion with heparinized saline, fixed by immersion in 100% methanol, dissected longitudinally, and imaged using a flatbed scanner.

NADPH-Diaphorase Staining

To determine localization of functional eNOS enzyme in the treated arteries, NADPH-diaphorase staining was performed on the cryo-sections of arteries obtained after 1, 7, and 21 days post-angioplasty. Frozen sections were permeabilized by incubating with 100 mmol/L Tris-HCl containing 0.2% v/v Triton X-100 (pH 8.0) for 10 min. The sections were stained by incubating with 1 mmol/L NADPH, 0.2 mM nitroblue tetrazolium in 100 mmol/L Tris-HCl containing 0.2% v/v Triton X-100 (pH 8.0) for 45 min at 37° C., washed thrice with PBS and mounted with glycerol for optical microscopy.

Statistical Analysis

All the data are presented as mean±standard error of means (S.E.M). The significance of differences between any two experimental groups was determined using the two-tailed Student's t test, and differences were considered significant at p values of <0.05.

Materials

Poly-(DL-lactide-co-glycolide) (PLGA, 50:50 lactide-glycolide ratio, inherent viscosity 1.32 dL/g in hexafluoro-isopropanol at 30° C.) was purchased from DURECT Corporation (Pelham, Ala.). Rat serum albumin (RSA, Fraction V), poly vinyl alcohol (PVA, average molecular weight 30,000-70,000), poly-L-lysine hydro bromide (PLL.HBr, average molecular weight 30,000-70,000), tartaric acid dimethyl ester (DMT), β-nicotinamide adenine dinucleotide 2'-phosphate reduced tetrasodium salt (β-NADPH), nitrotetrazolium blue chloride, Evan's blue, and radio immuno precipitation assay (RIPA) buffer were purchased from Sigma (St. Louis, Mo.). Recombinant human endothelial nitric oxide synthase (eNOS) was obtained from Axxora, LLC (San Diego, Calif.). Each batch of recombinant eNOS protein was provided (by Axxora LLC) with a concentration of more than 5 mg/ml and a specific activity of >0.1 nmol/mg/min (U/mg). Quantikine® human eNOS immunoassay kit was purchased from R&D Systems Inc. (Minneapolis, Minn.). BCA protein assay kit and ECL Western blotting substrate was purchased from Pierce (Rockford, Ill.). Precision Plus Protein™ dual color standards and horseradish peroxidase-conjugated goat anti-rabbit antibody were from Bio-Rad Laboratories (Hercules, Calif.). Rabbit polyclonal anti-eNOS antibody and mouse monoclonal anti-CD-45 antibody were purchased from BD Transduction Laboratories (San Diego, Calif.). Mouse monoclonal anti-tubulin, rabbit polyclonal anti-Ki-67 and rabbit polyclonal anti-smooth muscle actin antibodies were purchased from Abcam Inc. (Cambridge, Mass.). Mouse monoclonal anti-rat CD-68 antibody was obtained from Serotec Inc. (Raleigh, N.C.) and rabbit polyclonal anti-CD-31 antibody was purchased from Santa Cruz Biotechnology Inc. (Santa Cruz, Calif.). Protease inhibitor cocktail was from Calbiochem (Gibbstown, N.J.). KODAK BioMax MR film was purchased from Carestream Health Inc. (Rochester, N.Y.).

Formulation and Characterization of eNOS Protein-Loaded NPs

NPs containing eNOS protein were formulated with PLGA polymer using a double emulsion solvent evaporation technique. Vasir J K, Labhasetwar V., Biomaterials, 29:4244-52 (2008). In brief, 1 mg eNOS protein and 10 mg RSA were dissolved in 250 µl of 50 mmol/L triethanolamine buffer (pH 7.5, containing 0.5 mmol/L EDTA). The protein solution was emulsified into 1 ml of the polymer solution (27 mg PLGA polymer and 3 mg DMT in 1 ml of chloroform) using a probe sonicator (55 W for 1 min in an ice bath; Sonicator® XL, Misonix, Farmingdale, N.Y.). RSA was used in the formulation to stabilize eNOS protein from interfacial inactivation, and DMT was used to facilitate the release of the encapsulated protein from NPs. This primary water-in-oil emulsion was emulsified into 8 ml of an aqueous solution of PVA (2.0% w/v) and PLL (0.5% w/v), using the probe sonicator as above for 3 min to form a double water-in-oil-in-water emulsion. The double emulsion was stirred at room temperature for 2 hr, with continued stirring at 4° C. for ~18 hr and finally stirred under vacuum for 1 hr to evaporate the chloroform completely. NPs with entrapped protein were recovered by ultracentrifugation (30,000 rpm for 20 min at 4° C., Optima™ LE-80K, Beckman, Palo Alto, Calif.), and were subsequently lyophilized (−50° C. at a vacuum of 0.027 mBar, for 48 hr, FreeZone 4.5, Labconco, Kansas City, Mo.).

Characterization of Nanoparticles

Particle Size:

Particle size and polydispersity of NPs was determined using a ZetaPlus™ particle size analyzer (Brookhaven Instruments Corp., Holtsville, N.Y.). A suspension of NPs (0.1 mg/ml) was prepared in double-distilled water and sonicated for 30 s immersed in an ice bath.

Zeta Potential:

Zeta potential was measured as a function of pH to demonstrate the effect of pH on the surface charge of NPs. Buffers of pH 4.0 and 7.4 were prepared using a 1 mM hydroxyethyl piperazine ethane sulfonic acid (HEPES) solution and pH was adjusted with 0.1 N sodium hydroxide or hydrochloric acid solutions. NPs were suspended in the respective buffers (0.1 mg/ml), and zeta potential was measured using the ZetaPlus™ zeta potential analyzer (Brookhaven Instruments Corp., Holtsville, N.Y.).

Protein Loading:

The amount of eNOS protein loaded into NPs was determined from the total amount of protein added in the formulation and the protein that was not encapsulated into the NPs. The concentration of eNOS protein in the washings was determined by using the Quantikine® human eNOS immunoassay kit; the washings from the control NPs functioned as a blank.

Balloon Injury and Local Delivery of eNOS-NPs in Rat Model

Male Sprague Dawley rats (380 to 400 g, Charles River Laboratories, Wilmington, Mass.) were anesthetized with an intraperitoneal injection of mixture of ketamine (80 mg/kg) and xylazine (10 mg/kg). The left common carotid artery was exposed by blunt dissection through a midline neck incision under a dissection microscope. The left common, internal, and external carotid arteries were ligated with vessel clips to temporarily interrupt blood flow to the site of surgical manipulation. A 2F Fogarty balloon catheter (Edwards Life Sciences, Irvine, Calif.) was introduced in the left external carotid artery via an arterioctomy and it was advanced to the origin of the left common carotid artery. The balloon was inflated (with saline) sufficiently to generate slight resistance to the arterial wall and was withdrawn through the common carotid artery, followed by deflating the balloon. This procedure was repeated three times consistently to produce endothelial denudation of the entire length of the left common carotid artery. Upon removal of the balloon catheter, a PE 10 catheter was inserted into the left common carotid artery. The mid and the distal portions of the left common carotid artery and the left internal carotid artery were temporarily ligated. A suspension of NPs (210 µl saline containing 3 mg of eNOS-NPs which is equivalent to 72 µg of eNOS protein) was infused into the injured carotid artery over 5 min at 2 atm of pressure (three infusions of 70 µl each, with a 1 min period between infusions). Following infusion of NPs, the clips at the common and internal carotid arteries were released and the blood flow was restored. Locally infused NPs penetrate the injured artery through the disrupted endothelium. The inventors and others have shown site specific delivery in the target artery with almost undetectable levels in non-target artery. Joner et al., Arterioscler Thromb Vasc Biol., 28:1960-6 (2008); Panyam et al., FASEB J., 16:1217-26 (2002). Animals were randomly divided into three groups (n=6 animals per group), and received an infusion of (i) eNOS protein solution, (ii) a suspension of eNOS-NPs, (iii) Control NPs, and (iv) saline.

Vessel Harvest

Animals were euthanized at three weeks following vascular injury with an overdose of pentobarbital. All animals were transcardially perfused via the left ventricle for 2 min with heparinized saline, followed by 10% buffered formalin for another 5 min at physiological pressure. The carotid arteries were removed and kept in 10% formalin for 24 h. Following this, each artery was cut into three pieces every 5 mm from proximal to distal end, and all three pieces were then embedded in a single block of paraffin. Three serial sections (5 µm thick), sectioned at equally spaced intervals, were stained with hematoxylin and eosin (H&E) for morphometry and three additional similarly embedded sections (5 µm thick) were used for immunohistochemistry. For cryo-sections, the animals were perfused with heparinized saline as mentioned above, followed by 2% w/v solution of paraformaldehyde in phosphate-buffered saline (PBS). The arteries were fixed by immersion in ice-cold 2% w/v solution of paraformaldehyde at 4° C. for 1 hr. The arteries were then immersed in 5% w/v solution of sucrose in PBS for 30 min, 10% w/v solution of sucrose for 60 min and then stored overnight by immersing in a 20% w/v sucrose solution at 4° C. Arteries were then embedded in Tissue-Tek® O.C.T compound (Sakura, Torrance, Calif.) and stored at −80° C. until taken for histological evaluation. Serial sections (8 µm thick) were used for immunohistochemistry (CD-45 and CD-68) and NADPH-diaphorase staining. Images were acquired using a Leica DMR microscope (Leica Microsystems, GmbH, Wetzlar, Germany) equipped with Retiga EXi cooled CCD camera (QImaging, Surrey, BC, Canada) and analyzed using ImagePro Plus 6.1 software (MediaCybernetics, Bethesda, Md.). The number of positively stained cells were calculated in 9 serial sections per artery (n=3 to 6 rats per group). For Western Blotting, arteries were collected after perfusion with saline and snap-frozen until homogenization.

Morphometric Analysis

Morphometric analysis of the H&E stained arterial sections was performed via a computerized image analysis system (ImagePro Plus 6.1, MediaCybernetics, Bethesda, Md.). The quantitative measurements were made in a blinded manner of the areas corresponding to the internal and external elastic lamina and the lumen diameter. Three equally spaced cross sections were used in all rats to quantify the intimal lesions. The medial area was calculated by subtracting the area defined by the internal elastic lamina (IEL) from the area defined by the external elastic lamina (EEL) and the intimal area was determined by subtracting the lumen area from the area defined by the IEL. Finally, the intimal to medial area ratio (I/M) of each section was calculated.

eNOS Protein Levels by Western Blotting

To demonstrate sustained eNOS protein levels in the target artery, Western blotting was performed on artery homogenates collected at different time points. Snap-frozen arteries were homogenized in ice-cold RIPA lysis buffer supplemented with protease inhibitor cocktail. The homogenate was centrifuged at 14,000 rpm for 20 min at 4° C. and the supernatant was collected and processed for SDS-polyacrylamide gel electrophoresis (SDS-PAGE). BCA protein assay kit was used to determine the protein concentration in the homogenate samples. For each experiment, equal amounts of total protein (30 μg) were loaded into each lane and resolved by 8% SDS-PAGE under reducing conditions. Proteins were then blotted onto polyvinylidene fluoride (PVDF) membrane by semi-dry electroblotting (at 12 V, for 1 h). The membrane was incubated in blocking buffer containing 50 mmol/L Tris-HCl (pH 7.4), 500 mmol/L NaCl, 0.1% Tween-20 and 5% non-fat dried milk for 60 min under gentle agitation. Membranes were then incubated overnight at 4° C. with rabbit polyclonal anti-eNOS antibody (1:1000 dilution in blocking buffer). The membrane was washed in a buffer containing 50 mmol/L Tris-HCl (pH 7.4), 500 mmol/L NaCl, 0.1% Tween-20 and incubated with a 1:1000 dilution of secondary antibody (horseradish peroxidase-conjugated goat anti-rabbit antibody) in the blocking buffer for 1 h. The reaction products were detected by enhanced chemiluminescence using ECL Western blotting substrate. The signal was detected by exposure to KODAK BioMax MR film and quantified by densitometry. Prestained protein markers were used for molecular weight determinations and recombinant eNOS protein was used as the positive control. All membranes were also blotted for α-tubulin (using mouse monoclonal anti-tubulin antibody) to control for equal protein loading in all lanes.

Cell Culture

Human vascular smooth muscle cells (Cascade Biologics, Portland, Oreg.) were maintained on medium 231 supplemented with smooth muscle growth supplement (Cascade Biologics) at 37° C. in a humidified, 5% $CO_2$ atmosphere. Cells at passage 3-4 were typically used.

Intracellular Delivery of a Model Protein Using NPs

Cells (15,000 cells/mL/well) were seeded in 24-well plates and allowed to attach for 24 hr. To investigate the sustained activity of HRP enzyme-loaded NPs in comparison to HRP solution, cells were incubated with 4 μg/mL HRP (dissolved in cell culture medium) or 100 μg/mL of HRP-loaded NPs (equivalent to 4 μg HRP) for 24 hr. Medium was changed after 24 hr and then on every alternate day. After 1, 3, and 5 days, cells were washed twice with ice-cold PBS and lysed on ice in cell lysis buffer (50 mM Tris-HCl, pH 7.6, containing 1% TritonX-100). Cell lysates were centrifuged at 14,000 rpm at 4° C. for 10 min; the supernatants were analyzed for HRP activity using the SIGMAFAST™ OPD colorimetric assay (Sigma-Aldrich Co., St. Louis, Mo.). HRP concentrations in lysates were determined by comparing HRP activity in the lysate to a standard curve of purified HRP. This comparison of a standard curve of purified HRP prepared in cell lysis buffer to that prepared in the enzyme-free cell lysates indicated that the cell lysate components did not affect the determination of enzyme activity. The amount of active HRP was normalized to the total cell protein and expressed as nanograms per milligram of cell protein. Cells were grown on coverslips and treated with HRP-loaded NPs or HRP solution as described before, washed with PBS, fixed and incubated with $DAB/Ni^{2+}$ substrate (Vector Labs, Burlingame, Calif.) to stain active HRP enzyme present in the cells.

Arterial Uptake of NPs

To determine the arterial uptake of NPs in the target artery, a suspension of 6-coumarin labeled NPs was infused in injured rat carotid arteries (as described before) and animals were euthanized one hour after the infusion. Carotid arteries were removed, rinsed with saline, and then blotted dry using an absorbent paper. Wet weight of each artery was recorded, and artery was finely cut into small pieces with a scissor, homogenized in 2 ml of distilled water using a tissue homogenizer (Biospec Product Inc, Bartlesville, Okla.) at 1,000 rpm for 2 min, and the homogenates were lyophilized for 48 hrs. The fluorescent dye from the NPs in the artery homogenates was extracted by shaking lyophilized samples with 1 ml of dichloromethane at 37° C. for 24 hrs at 150 rpm using an Environ® orbital shaker (Lab Line, Melrose Park, Ill.). The extracts were centrifuged at 14,000 rpm for 10 min (Eppendorf Microcentrifuge, 5417R, Brinkmann Instruments, Westbury, N.Y.) to remove cell debris. The supernatants were analyzed for the dye content by HPLC, as previously described. Panyam et al., J Drug Target., 10:515-23 (2002).

Results

Formulation and Characterization of eNOS-NPs

Figure 1B:
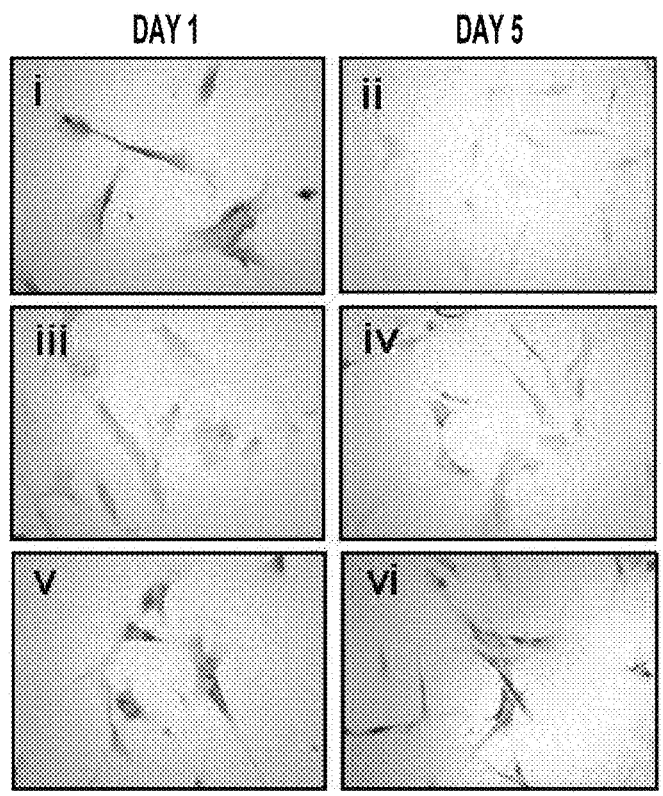

PLL-functionalized NPs encapsulating eNOS protein were spherical in shape with a mean hydrodynamic size of 260±20 nm, polydispersity index<0.20, and zeta potential (surface charge) of −12 mV at pH 7. The mean particle size by transmission electron microscopy was 81±4 nm. Reddy et al., Appl Biochem Biotechnol., 151 (2-3):565-77 (2008). eNOS protein loading in NPs was 1.2% w/w (i.e., 100 mg of NPs contained 1.2 mg of eNOS protein), with an encapsulation efficiency of 99% as determined using eNOS immunoassay. To evaluate the efficiency of our functionalized NPs to deliver bio-active protein intracellularly, NPs encapsulating horse radish peroxidase (HRP) were formulated; as with HRP, the protein levels in cells can be quantitated and visualized by staining. The amount of HRP loaded into NPs and that released from NPs was the same for both unmodified and functionalized NPs. HRP-loaded functionalized NPs demonstrated 50-fold greater enzyme activity in VSMCs as compared to that with unmodified NPs and protein in solution, and functionalized NPs maintained the enzyme activity in cells during the experimental period of one week (FIG. 1a-b). Further, functioned NPs showed 3-fold greater arterial uptake than unmodified NPs at 1 hr following localized delivery in rat carotid artery model.

Inhibition of Neointimal Hyperplasia

Morphometric analysis demonstrated significant reduction (60%) in intimal hyperplasia in the eNOS-NP treated group than in saline control animals (Intima to Media ratio, I/M=1.15±0.10 vs. Control NPs, 2.05±0.09; Saline, 2.81±0.27; p<0.005) (FIG. 2a-f) with a concomitant increase in lumen area (0.200±0.018 mm$^2$ vs. Saline Control 0.095±0.004 mm$^2$; p<0.005) (FIG. 2g). There was no significant difference between saline and control NPs treated animals (I/M=Control NPs, 2.05±0.09; Saline, 2.81±0.27; p=0.04). Animals treated with eNOS protein solution showed a marginal reduction in hyperplasia (27%) compared to saline control (I/M=2.06±0.07 vs. 2.81±0.27; p=0.04). No statistically significant difference was found between the medial areas, EEL circumference and EEL areas for uninjured contralateral arteries and injured arteries in saline control, or treated with eNOS-NPs or eNOS-solution. Therefore, it appears that eNOS-protein delivery had minimal effect on adaptive vascular remodeling but had a significant effect on inhibiting neointimal hyperplasia.

Proliferation Index of Smooth Muscle Cells

The arterial sections obtained from rats at 3 wk post-angioplasty were immunostained for α-SMA (marker for VSMCs). Majority of cell population present in neointima stained positive for α-SMA, thus demonstrating that the hyperplasia was due to migration and proliferation of VSMCs (FIG. 3a-c). To determine the mechanism of inhibition of VSMC proliferation with eNOS protein delivery, the arterial sections were immunostained for Ki-67 (marker for proliferating cells) (FIG. 3d-f). Ki-67 is a nuclear antigen expressed by cells in all the phases of active cell cycle/proliferation (G1, S, G2 and M phase). Arterial sections from the animals treated with saline and eNOS protein solution showed positive staining for Ki-67 (brown immunostaining overlapping with blue (hematoxylin) counter-stained for nucleus) (FIGS. 3g and 3h), indicating that cells were in an active proliferation stage of cell cycle. In contrast, the sections from the eNOS-NPs treated group showed significantly fewer cells which were positive for Ki-67 (FIG. 3i), indicating that the cells were in resting G0 phase of cell cycle. Proliferation index was calculated as the percentage of total cells that were Ki-67 positive. The results demonstrated significant reduction in the percentage of proliferating cells in the arteries treated with eNOS-NPs as compared to that in saline control (32±4 vs. 95±2; p<0.005) (FIG. 3j) or eNOS protein solution (80±8 vs. 95±2; p=0.12).

Inhibition of Leukocyte/Macrophage Infiltration

Analysis of the arterial sections 24 h following the angioplasty procedure demonstrated a significant reduction in the recruitment of leukocytes (eNOS-NPs, 163±20 vs. saline, 392±74 CD-45 positive cells/section) (FIG. 4a-c, 4g) and infiltration of macrophages (eNOS-NPs, 143±22 vs. saline, 274±6 CD-68 positive cells/section) (FIG. 4d-f, 4h) in eNOS-NP treated group than in saline control.

Re-Endothelialization of Denuded Carotid Artery

Figures 6A, 6B, 6C:
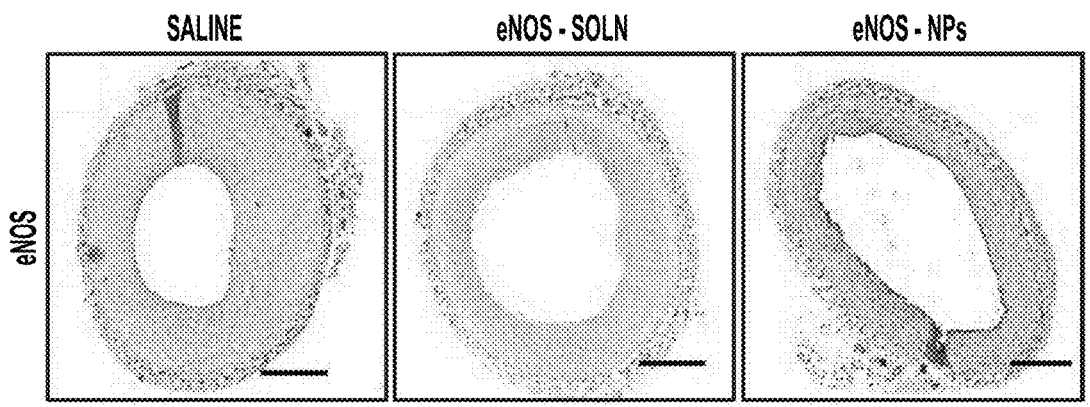
FIG. 6A-FIG. 6F provide images showing the functional recovery of injured endothelium. (A-F) Immunostaining for eNOS. Representative arterial sections from the group: saline (A and D), eNOS protein solution (B and E), and eNOS-NPs (C and F) stained for eNOS after 3 wk of vascular injury. Figure (D), Figure (E), and Figure (F) (scale bar=50 μm) are magnified images of Figure (A), Figure (B), and Figure (C) (scale bar=200 nm), respectively. Brown staining represents immuno-stained eNOS, while all nuclei were counterstained (blue) with hematoxylin. Only a few cells lining the arterial lumen stained positive for eNOS in saline (D), while eNOS activity was detected in small patchy areas lining the lumen of artery in eNOS protein solution treated arteries (E). In arteries treated with eNOS-NPs (F), immuno-active eNOS protein was detected in VSMCs present in the medial layer as well as in almost 95% of cells lining the lumen of artery.
Figures 6D, 6E, 6F:
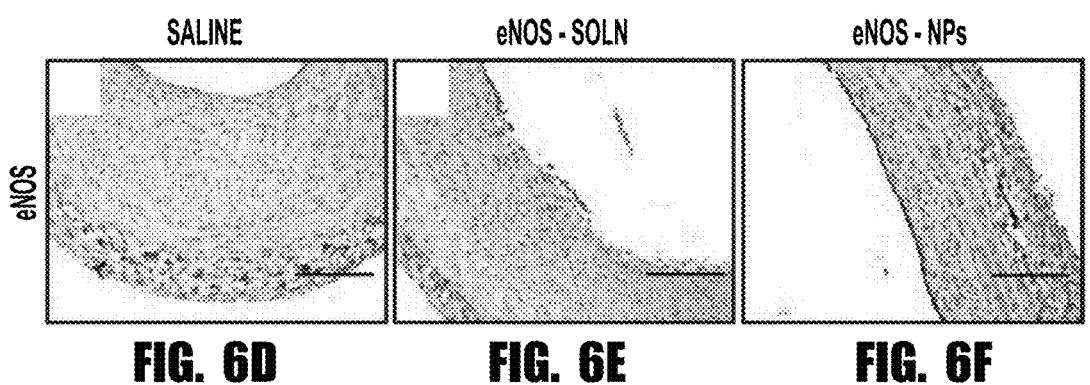

Staining of the arterial sections for CD-31 from the animals treated with eNOS-NPs demonstrated significantly greater re-endothelialization of the injured artery than in saline control animals (91% vs. 34%; p<0.001) (FIG. 5 a-g). eNOS protein solution was ineffective in inducing re-endothelialization, and the results were almost similar to saline control (41% vs. 34%; p=0.44) (FIG. 5g). Re-endothelialization was further evident from the reduced extravasation of Evan's blue dye in eNOS-NP treated group than in saline control (FIG. 5h,i). To assess the functional recovery of the newly formed endothelium, the sections were immunostained for eNOS using an isoform-specific antibody that showed significantly higher number of cells (95%) for eNOS activity whereas only few cells showed the enzyme activity in saline control (FIG. 6a-f). In addition, eNOS immunoreactivity was detectable in the medial layer of arteries from the animals treated with eNOS-NPs but not in other groups (FIG. 6f).

NOS Activity in Treated Artery

Figure 7A:
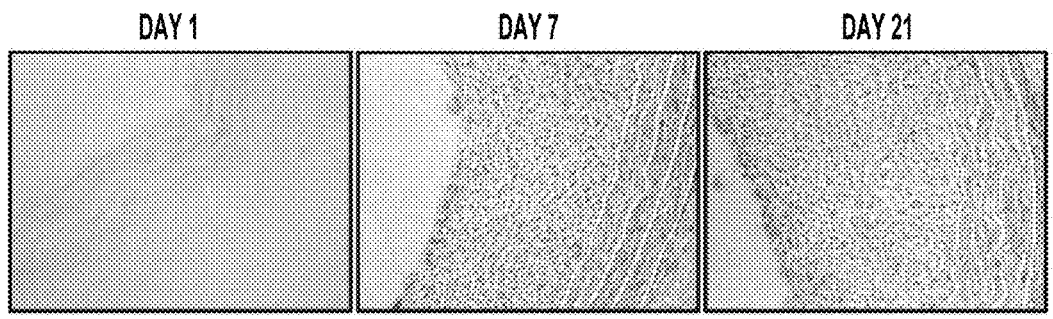
FIG. 7A-FIG. 7D provide graphs and images showing the sustained delivery of eNOS protein via eNOS-NPs. Representative arterial sections (400×) stained for NADPH-diaphorase activity in saline (A) and eNOS-NPs (B) treated group. eNOS protein levels were determined by Western blotting of the artery homogenates (C). Lanes (1) uninjured artery, (2) injured, saline treated 1 wk, (3) injured, eNOS-NPs treated 1 wk, (4) injured, saline treated 3 wk, (5) injured, eNOS-NPs treated 3 wk, and (6) recombinant eNOS protein (positive control). Results of Western blotting indicated in arbitrary densitometric unite, as a ratio of eNOS protein to that of tubulin (loading control) (D). UI: uninjured artery, S1: saline treated at 1 wk, N1: eNOS-NPs treated at 1 wk, S3: saline treated at 3 wk, N3: eNOS-NPs treated at 3 wk.
Figure 7B:
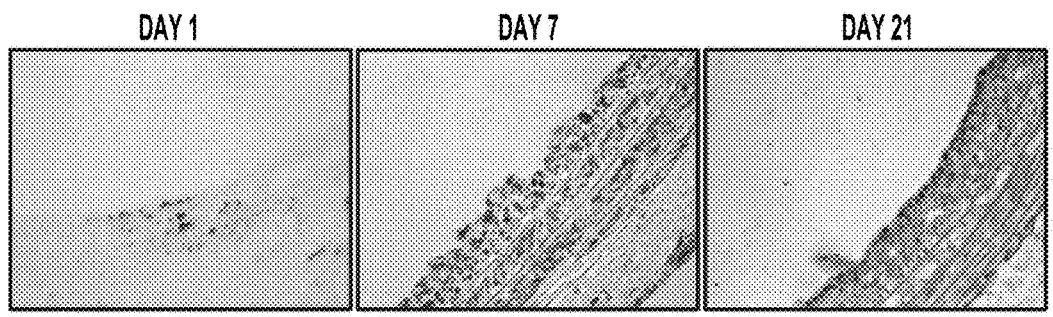
Figure 7C:
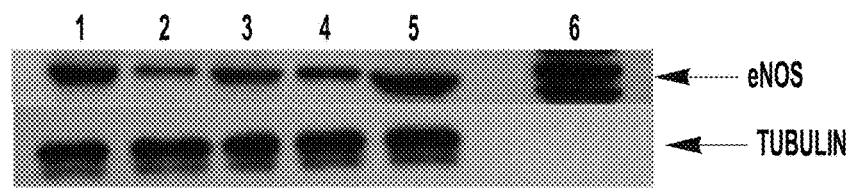
Figure 7D:
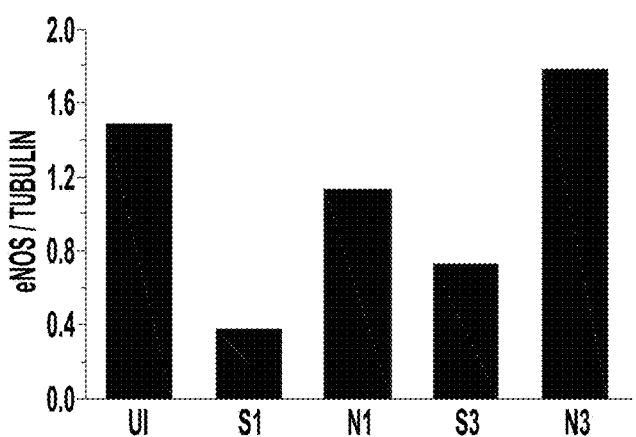

NADPH-diaphorase staining was used to determine localization of functional NOS protein in the arterial wall. This method detects the diaphorase activity of eNOS that involves catalysis of NADPH oxidation using an electron acceptor (tetrazolium salt) whereby the latter is reduced to a purple-colored insoluble formazan derivative. At day 1, the arteries from the eNOS-NPs treated group showed the presence of NOS activity localized in the medial layer; however, at 7 days, the sections showed intense NADPH-diaphorase staining. The arterial sections obtained at 3 wk demonstrated NOS activity in the endothelial layer formed in the eNOS-NP treated group; while the arteries from saline control showed faint staining. These results, thus demonstrate the sustained activity of eNOS protein in the eNOS-NP treated group (FIG. 7a-b).

Quantitative Determination of eNOS Protein in the Treated Arteries eNOS protein levels were determined by Western blotting of the arterial homogenates from eNOS-NP treated group. Significant levels of immunoreactive eNOS protein was detected 7 days; while the arteries saline control showed minimal eNOS levels (FIG. 7 c-d). Level of eNOS protein in the arteries from the eNOS-NP treated animals was comparable to that present in uninjured (contralateral) artery.

Discussion

The inventors have demonstrated that the localized and sustained delivery of recombinant eNOS protein inhibit intimal hyperplasia and re-endothelialize the injured artery. Sustained presence of eNOS activity restored the vasoprotective functions of endothelium, inhibited the recruitment of leukocytes and macrophages, and also prevented uncontrolled proliferation of VSMCs in response to vascular injury. Endothelium, the inner most layer of cells lining the lumen of blood vessels, plays a significant role in vascular homeostasis and pathogenesis of many diseases. The predominant functions of endothelium include maintenance of vascular tone, preventing thrombogenicity, and regulation of VSMC proliferation. Garg U C, Hassid A., J Clin Invest., 83:1774-7 (1989). Endothelial cells exert most of these functions by producing a diverse array of regulatory proteins and other paracrine substances (such as prostacyclin, tissue plasminogen activator, transforming growth factor-beta 1 (TGF-β1, NO etc.). One of the major regulatory proteins produced by endothelial cells is eNOS enzyme that catalyzes the NADPH and oxygen dependent oxidation of L-arginine to L-citrulline and NO. Cooke J P, Dzau V J., Annu Rev Med., 48:489-509 (1997). In addition to its role as the most potent endogenous vasodilator, NO also acts in consort with TGF-β1 to keep the underlying VSMCs in a quiescent state. Endothelial denudation following balloon angioplasty leads to the loss of vasoprotective factors such as eNOS, resulting in vascular deficiency of NO levels at the site of injury. This triggers the process of hyperplasia via leukocyte adherence to the vessel wall and production of mitogenic factors, resulting in proliferation of VSMCs. Further, the lack of re-endothelialization has been suggested to be the main cause for occurrence of thrombosis and rebound of hyperplasia in patients treated with drug eluting stents. NP-mediated localized and sustained delivery of recombinant eNOS protein is a potential approach to augment NO levels in the injured vessel wall following balloon angioplasty.

Delivery of recombinant proteins is limited by their short plasma half-life (due to proteolytic degradation) and limited cellular uptake (due to high molecular weight). Localized protein (e.g., recombinant apolipoprotein A and hepatocyte growth factor) delivery via intra-mural delivery or using infusion pumps was ineffective because of the above factors. Kaul et al., Circulation, 107:2551-4 (2003); Yasuda et al., Circulation, 101:2546-9 (2000). PLGA-NPs can protect the encapsulated protein from proteolysis and release it in a sustained manner (Davda J, Labhasetwar V., J Biomed Nanotechnology, 1:74-82 (2005)); however, endosomal sequestration and exocytosis could limit the efficacy of NPs for intracellular delivery of therapeutics. Panyam J, Labhasetwar V., Pharm Res., 20:212-20 (2003); Panyam et al., FASEB J., 16:1217-26 (2002). To address these issues, PLL-functionalized PLGA-NPs were developed, which previous studies by the inventors have shown to result in significantly higher cytoplasmic delivery of bio-active protein than that with unmodified NPs because of their greater cellular delivery and escape from the endosomal compartment (FIG. 1). Despite modification with cationic PLL, the formulation parameters were optimized so that functionalized NPs remain negatively charged at physiologic pH to avoid interactions with serum proteins and possibility of aggregation following in vivo administration.

Functionalized NPs facilitated sustained release of bioactive eNOS enzyme in the treated arteries up to 3 wks post-angioplasty. In addition, a fraction of NPs could have been deposited in the arterial wall via their transport through vasa vasorum (Rome et al., Arterioscler Thromb. 14:148-61 (1994)), which are small capillaries originating from the lumen of the artery with a network spreading to adventitia and media. Gossl et al., Am J Physiol Heart Circ Physiol. 287:H2346-51 (2004). Following angioplasty, NPs were primarily taken up by VSMCs and demonstrated the presence of eNOS activity. For eliciting its activity, eNOS requires a cofactor, tetrahydrobiopterin (BH4), the basal level of which is shown to be sufficient enough in VSMCs to support the eNOS activity. Kullo et al., Arterioscler Thromb Vasc Biol., 17:2405-12 (1997). NADPH-diaphorase staining shows eNOS activity primarily in the vicinity of NPs localized in the vessel wall at 1 day post-angioplasty (FIG. 7b). However, the extensive diaphorase staining seen at day 7 and 21 could be due to the release of the encapsulated eNOS, thus sustaining the biological activity of the enzyme in the artery (FIG. 7b). Though diaphorase staining does not give isoform specific activity, the arteries from saline control showed minimal to no staining at any time points (FIG. 7a), which is in agreement with the previous studies by others that did not show immunostaining for the inducible NOS (iNOS) after 5 and 14 days of balloon angioplasty in rat carotid artery model. Janssens et al., Circulation, 97:1274-81 (1998). Western blotting provides a second confirmation of sustained presence of eNOS protein in the arteries from eNOS-NP treated group (FIG. 7c-d). eNOS-immunostaining of the arterial sections obtained at 3 wk post-angioplasty also showed the presence of eNOS protein in the medial layers of arteries from eNOS-NP treated group (FIG. 6f) while no eNOS protein was detected in the arteries from eNOS-solution or saline control animals. These results demonstrate the ability of NPs to maintain eNOS activity in the treated artery.

Most of the therapeutic strategies focus on acceleration of re-endothelialization using growth factors (such as vascular endothelial growth factor: VEGF (Asahara et al., Circulation. 91:2793-801 (1995)), basic fibroblast growth factor: b-FGF (Lindner et al., J Clin Invest. 85:2004-2008 (1990)), etc.) but these could cause hyperplasia. eNOS enzyme delivery with NPs inhibited the basic pathways of inflammation as evident from the immunohistochemical analysis of the arterial sections collected at 24 hr demonstrated significant reduction of infiltration of macrophages and leukocytes at the injured site (FIG. 4g-h). Similar reduction in inflammatory response to vascular injury has been observed after treatment with NO releasing aspirin adducts in femoral arteries of hypercholesterolemic ApoE (−/−) mice. Yu et al., Lab Invest., 82:825-32 (2002). Further, the arteries from eNOS-NP treated group stained for Ki-67 showed a significant inhibition of proliferation of VSMCs as compared to that in eNOS-solution and saline controls (FIG. 3j). This anti-proliferative effect of eNOS protein is manifested by the production of NO, which is known to reduce cell proliferation via upregulation of cell cycle inhibitory molecules (such as p21 and p27). Sato et al., Cardiovasc Res., 47:697-706 (2000). Also, NO is known to reduce VSMC proliferation through a cGMP-dependent mechanism or cGMP-independent pathways. Ignarro et al., Proc Natl Acad Sci USA., 98:4202-8 (2001). Since Ki-67 is a marker for cells in an active phase of cell cycle; it appears that the anti-proliferative effect of eNOS was mediated by a delay in cell cycle progression and thereby most cells were arrested in G0 phase. Further, the results from Evan's blue dye exclusion, CD-31 and eNOS immunostaining, and diaphorase activity staining confirm the integrity as well as functional recovery of the endothelium generated in animals treated with eNOS-NPs. Cooney et al., Gene Ther., 14:396-404 (2007). The eNOS delivery may create conducive conditions by inhibiting the infiltration of inflammatory cells at the injured site that could have favored a local process involving endothelial proliferation and migration adjacent to the site of injury. Van Belle et al., Cardiovasc Res., 38:54-68 (1998). The other possibility is that NO could have facilitated the homing of endothelial progenitor cells (EPCs) at the injury site and contributed towards re-endothelialization process. Iwakura et al., Circulation, 108:3115-21 (2003).

In normal rat carotid artery injury model, the data provide evidence that eNOS protein delivery inhibits the basic pathways (inflammation and proliferation of VSMCs) responsible for hyperplasia, and hence this therapeutic strategy is expected to effective in atherosclerotic condition as well. Moreover, recently Sharif et al. have demonstrated almost the same degree of inhibition of hyperplasia and re-endothelialization with eNOS gene coated stents in both normocholesterolemic and hypercholesterolemic rabbits. Sharif et al., Mol Ther., 16:1674-80 (2008).

Our approach is feasible to use in a clinical setting, as NPs can be infused into vasculature using a catheter, either alone or in conjunction with a stent (either coated on stent or infused locally following stenting) to facilitate re-endothelialization while inhibiting hyperplasia. Sustained eNOS protein therapy could be effectively used in other vascular disorders which primarily involve genetic or pathophysiological loss of eNOS such as hypercholesterolemia, atherosclerosis, hypoxia-induced pulmonary hypertension, etc., signifying the broader applications of eNOS-loaded NPs.

Example 2: Procedure for Coating a Stent and Balloon with Nanoparticles

Nanoparticles containing bovine serum albumin (BSA) as a model protein and SDB5700 dye as a near-infrared (NIR) marker were formulated with 1.32 d l/g poly dl-lactide co-glycolide (PLGA) polymer using a double emulsion technique. Aqueous BSA solution at a concentration of 1 mg/15 µl was emulsified into a 15.25 mg/ml solution of PLGA in chloroform containing 16.7 µl of SDB5700 NIR dye. Emulsification was performed using a probe sonicator (55 W for 2 minutes in an ice bath; Sonicator XL, Misonix, Farmingdale, N.Y.). The primary emulsion was then added to 4 ml of an aqueous solution of the emulsifier poly (vinyl alcohol) (PVA) and the surface charge modulatory poly-L-lysine (PLL) (PVA to PLL ratio 2 to 0.5 w/w). The mixture was then vortexed for 3 minutes and then sonicated as above for 5 minutes to form a double water-in-oil-in-water emulsion. The double emulsion was then centrifuged for 10 minutes at 1,000 rpm and the top layer was saved for application. Particle sizing was then performed using Nicomp particle sizing system confirming nanoparticle production (NICOMP 380 ZLS; Santa Barbara, Calif.). In order to coat the above emulsion on stent or balloon surface evenly, it was rotated at approximately 200 rpm. Next, the emulsion was applied using a Paasche VL double action siphon feed airbrush (airbrush settings: 50 psi, nozzle closed, top adjustment wheel between ¼ and ½ turn open, 6 inch working distance from sample). Each coat consisted of 30 seconds with 20 minutes between coats to ensure sufficient drying. Nanoparticles are formed in situ onto stent or balloon surface following evaporation of solvents (chloroform and water).

Imaging with Maestro which detects a near-infrared signal showed coated and uncoated ends of the same stent (FIG. 8a). The image through the top of the stent showed that the inside of the stent is also coated (FIG. 8b). The scanning electron microscopy showed deposition of nanoparticles onto the stent surface (FIG. 8c). Nanoparticles are seen embedded into the polyvinyl alcohol (PVA), which is used as an emulsifier. Imaging of the coated balloon show fluorescence signal of nanoparticles; there is no signal from uncoated balloon (FIG. 8d). The same procedure has been tested for coating of nanoparticles on a vascular graft The complete disclosure of all patents, patent applications, and publications, and electronically available materials cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A sustained-release composition for stimulating endothelial cell growth, comprising a nitric oxide synthase dispersed within the matrix of a biocompatible polymeric nanoparticle.

2. The sustained-release composition of claim 1, wherein the nitric oxide synthase is endothelial nitric oxide synthase.

3. The sustained-release composition of claim 1, further comprising albumin within the nanoparticle matrix.

4. The sustained-release composition of claim 1, wherein the biocompatible polymer is a biodegradable polymer.

5. The sustained-release composition of claim 1, wherein the biocompatible polymer is poly-(DL-lactide-co-glycolide).

6. The sustained-release composition of claim 1, wherein the composition further comprises one or more nitric oxide synthase cofactors.

7. The sustained-release composition of claim 1, wherein the nanoparticle is a surface modified nanoparticle.

8. The sustained-release composition of claim 1, wherein the nanoparticle has a diameter from 10 to 300 nanometers.

9. A method of inducing endothelium formation in a blood vessel, comprising contacting the blood vessel with a nanoparticle comprising nitric oxide synthase dispersed within the matrix of a biocompatible polymeric nanoparticle.

10. The method of claim 9, wherein the nitric oxide synthase is endothelial nitric oxide synthase.

11. The method of claim 9, further comprising albumin within the nanoparticle.

12. The method of claim 9, wherein the biocompatible polymer is a biodegradable polymer.

13. The method of claim 9, wherein the biocompatible polymer is poly-(DL-lactide-co-glycolide).

14. The method of claim 9, wherein the nanoparticle is a modified nanoparticle.

15. The method of claim 9, wherein the endothelium formation is induced in a subject to treat or prevent negative remodeling, thrombosis, vascular fibrosis, inflammation, platelet aggregation, hyperplasia, or restenosis of the blood vessel of the subject.

16. The method of claim 15, wherein the subject has been diagnosed as having diabetic nephrophathy.

17. The method of claim 15, wherein the subject has been diagnosed as having a renal or hepatic disease involving endothelial dysfunction.

18. An implantable or deliverable medical device coated with a sustained-release composition for stimulating endothelial cell growth, comprising a nitric oxide synthase dispersed within the matrix of a biocompatible polymeric nanoparticle.

19. The implantable or deliverable medical device of claim 18, wherein the nitric oxide synthase is endothelial nitric oxide synthase.

20. The implantable or deliverable medical device of claim 18, further comprising albumin within the nanoparticle.

21. The implantable or deliverable medical device of claim 18, wherein the biocompatible polymer is a biodegradable polymer.

22. The implantable or deliverable medical device of claim 18, wherein the biocompatible polymer is poly-(DL-lactide-co-glycolide).

23. The implantable or deliverable medical device of claim 18, wherein the implantable medical device is configured to fit within a blood vessel.

24. The implantable or deliverable medical device of claim 23, wherein the implantable medical device is selected from the group consisting of vascular grafts, stents, and balloon catheters.

* * * * *